US009243659B2

(12) United States Patent
Raybuck

(10) Patent No.: US 9,243,659 B2
(45) Date of Patent: Jan. 26, 2016

(54) SYSTEMS AND METHODS FOR COMPOSITE FRAME SYSTEMS

(71) Applicant: Alcon Research, Ltd., Fort Worth, TX (US)

(72) Inventor: John L. Raybuck, Painesville, OH (US)

(73) Assignee: Alcon Research, Ltd., Fort Worth, TX (US)

( * ) Notice: Subject to any disclaimer, the term of this patent is extended or adjusted under 35 U.S.C. 154(b) by 0 days.

(21) Appl. No.: 14/471,049

(22) Filed: Aug. 28, 2014

(65) Prior Publication Data

US 2015/0050099 A1 Feb. 19, 2015

Related U.S. Application Data

(63) Continuation of application No. 12/635,070, filed on Dec. 10, 2009, now Pat. No. 8,851,308.

(51) Int. Cl.

| F16B 39/00 | (2006.01) |
|---|---|
| F16B 39/282 | (2006.01) |
| B29C 65/00 | (2006.01) |
| F16L 13/16 | (2006.01) |
| B29C 45/14 | (2006.01) |
| A61B 19/02 | (2006.01) |
| A61B 17/00 | (2006.01) |

(52) U.S. Cl.
CPC ............ *F16B 39/282* (2013.01); *A61B 19/0248* (2013.01); *B29C 45/14614* (2013.01); *B29C 66/52441* (2013.01); *F16L 13/161* (2013.01); *A61B 2017/00199* (2013.01); *A61B 2019/025* (2013.01); *A61B 2019/0249* (2013.01); *Y10T 29/49826* (2015.01)

(58) Field of Classification Search
CPC .... F16B 12/40; F16B 12/42; F16B 2012/403; F16B 2012/406; F16B 39/00; F16B 39/282
USPC .................................. 411/259, 548; 211/182
See application file for complete search history.

(56) References Cited

U.S. PATENT DOCUMENTS

| 3,339,609 | A | * | 9/1967 | Cushman ..................... 411/82.1 |
|---|---|---|---|---|
| 3,936,111 | A | * | 2/1976 | Mazzucconi .............. 312/265.4 |
| 4,973,208 | A | * | 11/1990 | Gauron ........................ 411/82.1 |
| 6,371,313 | B1 | * | 4/2002 | Walter et al. ................. 211/123 |
| 6,789,993 | B2 | * | 9/2004 | Ozawa et al. ................. 411/546 |
| 7,857,565 | B2 | * | 12/2010 | Martinson ..................... 411/136 |
| 7,891,927 | B2 | * | 2/2011 | Burger et al. ................ 411/546 |
| 8,251,725 | B2 | * | 8/2012 | Kasparian et al. ............. 439/252 |
| 8,651,787 | B2 | * | 2/2014 | Levey et al. ................. 411/180 |

* cited by examiner

*Primary Examiner* — Roberta Delisle

(57) ABSTRACT

In various embodiments a frame system for a surgical system may include a plurality of rod structures cross connected through one or more structural members. In some embodiments, the rod structures may each include at least one rod with an interface joint molded over the at least one rod. One or more of the interface joints may include a receiving hole for receiving a structural member to couple at least two of the plurality of rod structures together. One or more surgical components (such as a surgical console) may be received into the frame system. Other components may also be received into the frame system (e.g., an aesthetic skin). The rod structures may also include cross face structural members that are secured to portions of the rod structures through being molded to the rod structures through the interface joints.

7 Claims, 38 Drawing Sheets

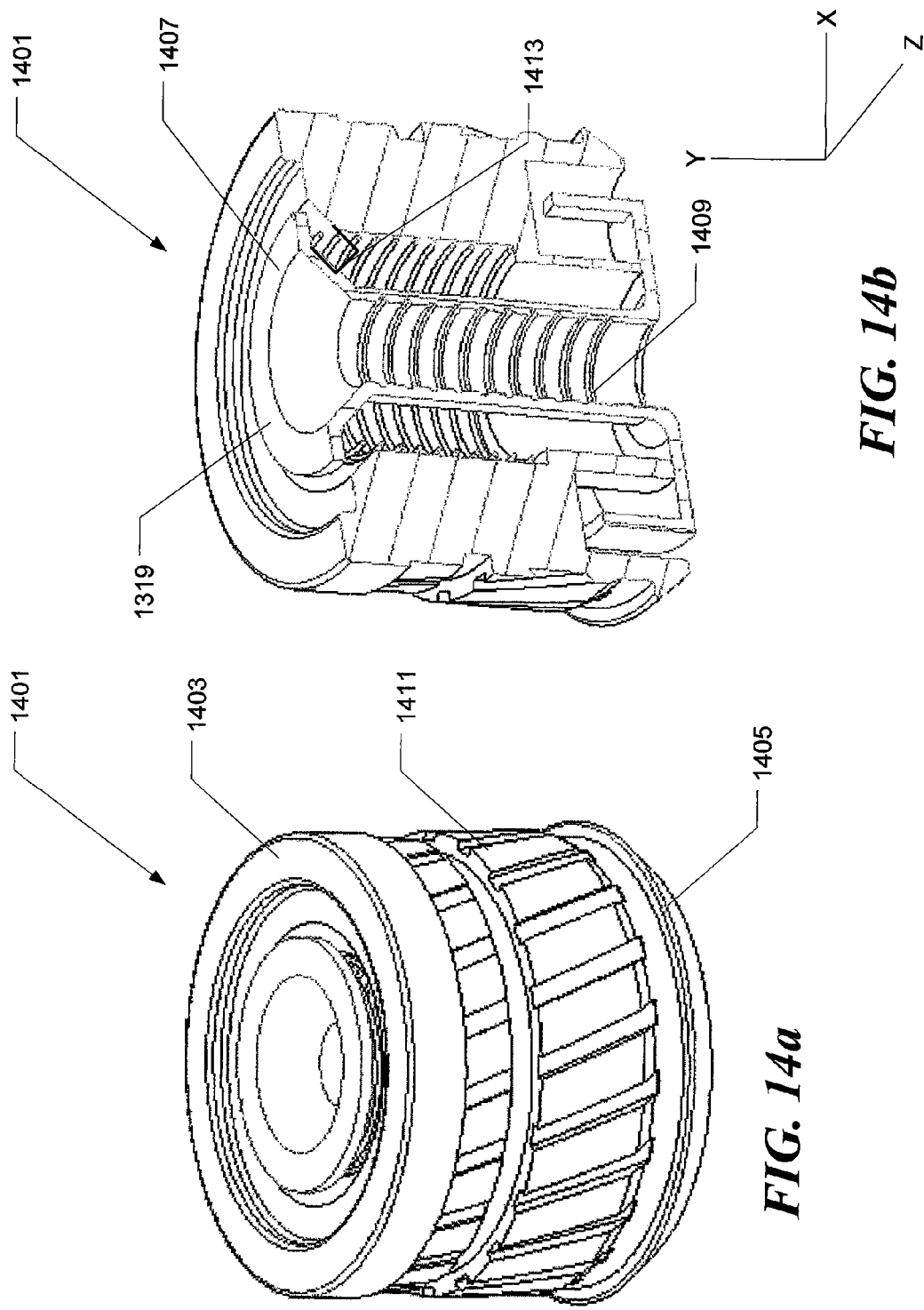

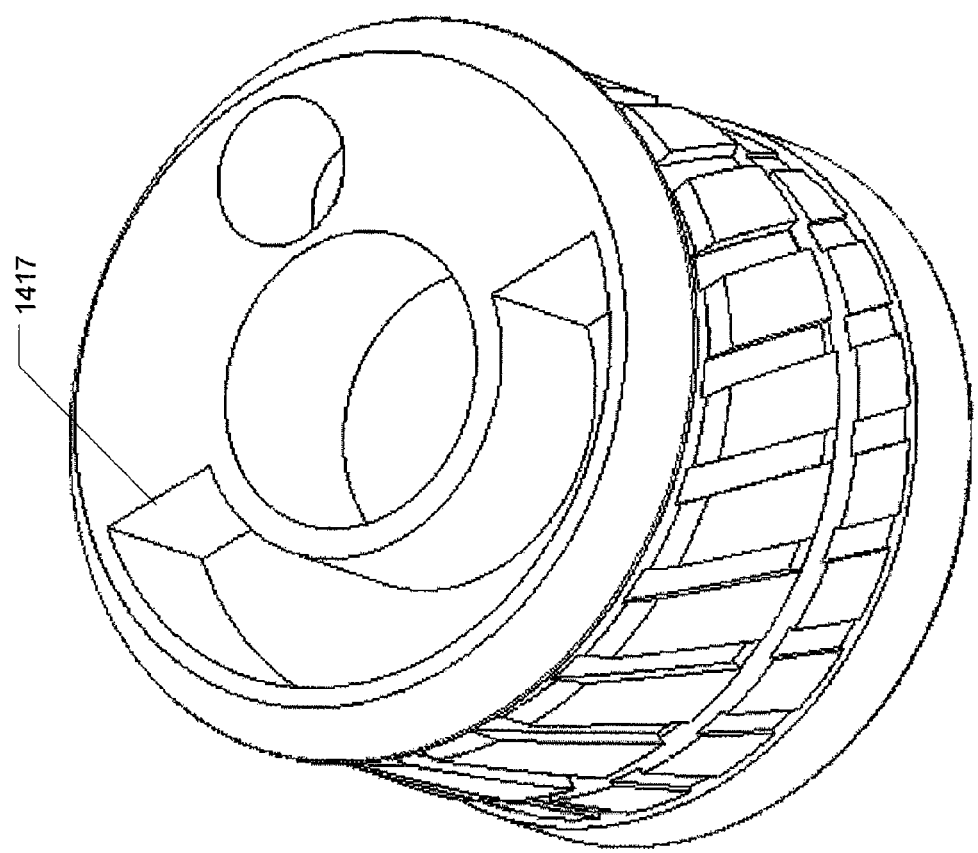

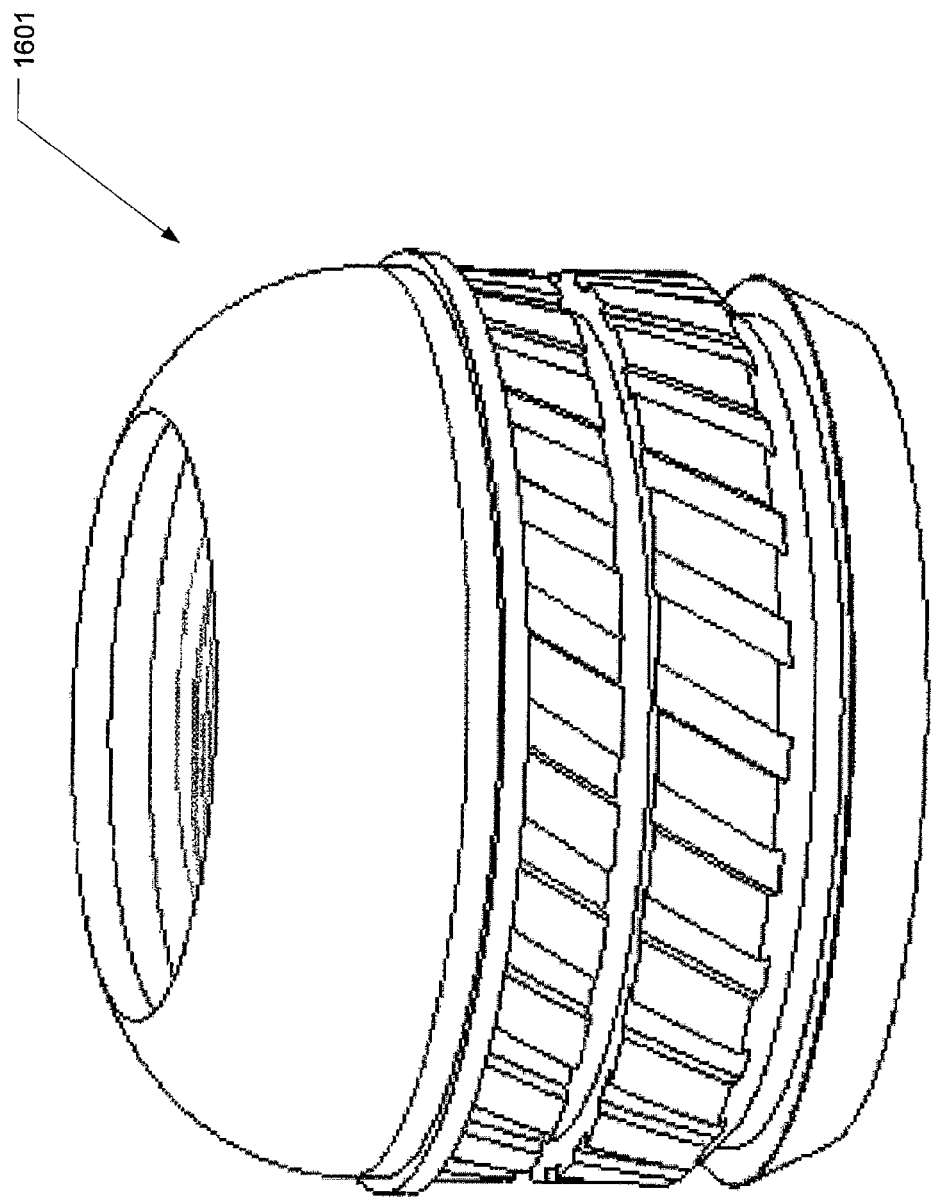

SYSTEMS AND METHODS FOR COMPOSITE FRAME SYSTEMS

PRIORITY CLAIM

This application is a continuation application of U.S. patent application Ser. No. 12/635,070 titled "Systems and Methods for Composite Frame Systems" which was filed Dec. 10, 2009, whose inventors are John L. Raybuck and Long Q. Nguyen which is hereby incorporated by reference in its entirety as though fully and completely set forth herein.

FIELD OF THE INVENTION

The present invention generally pertains to support structures. More particularly, but not by way of limitation, the present invention pertains to support structures for surgical consoles.

DESCRIPTION OF THE RELATED ART

Various support structures for the storage and transportation of surgical consoles have been used in the past. Simple, open support structures with several, stacked shelves are sometimes used. The support structures may be made from metal or plastic, and may employ solid shelves or shelves formed from spaced, parallel members. Such support structures may not be specifically designed for the surgical console they serve, and may provide little, if any, protection for the ancillary equipment and consumables that are used with the surgical console.

Other support structures have been designed for medical applications. These support structures may have an external surface for supporting a surgical console, an internal frame made from metal with shelves and/or drawers to store the ancillary equipment and consumables used with the surgical console, and an outer housing disposed over the internal frame. The outer housing may be constructed of multiple sheets of sheet metal or multiple plastic components (e.g., made from such methods as structural foam molding, injection molding, gas-assist injection molding and thermoforming) fastened together with screws, rivets, or other conventional fastening apparatus. The sheet metal or plastic components may be painted to provide a chemically resistant and aesthetically pleasing external surface.

SUMMARY OF THE INVENTION

In various embodiments a frame system for a surgical system may include a plurality of rod structures cross connected through one or more structural members. In some embodiments, the rod structures may each include at least one rod with an interface joint molded over the at least one rod. One or more of the interface joints may include a receiving hole for receiving a structural member to couple at least two of the plurality of rod structures together. One or more surgical components (such as a surgical console) may be received into the frame system. Other components may also be received into the frame system (e.g., an aesthetic skin).

In some embodiments, the rod structures may include an attachment point (e.g., a dimple) at the portion of the rod structure receiving an interface joint to better secure the interface joint to the rod structure. The rod structures may also include cross face structural members that are secured to portions of the rod structures through being molded to the rod structures through the interface joints. In some embodiments, these cross face structural members may be plugged on an end that engages the interface joint to avoid molding material flowing into the interior of the cross-face structural member during the molding process. In some embodiments, portions of the rod structures, cross-face structural members, and/or other structural members may be inserted into the interface joints after formation of the interface joints (and secured thereto through, for example, adhesive, snap fit, or a friction fit).

BRIEF DESCRIPTION OF THE DRAWINGS

For a more complete understanding of the present invention, reference is made to the following description taken in conjunction with the accompanying drawings in which:

FIGS. 13a-16h illustrate inserts, according to various embodiments;

It is to be understood that both the foregoing general description and the following detailed description are exemplary and explanatory only and are intended to provide a further explanation of the present invention as claimed.

DETAILED DESCRIPTION OF THE EMBODIMENTS

Figure 1A:
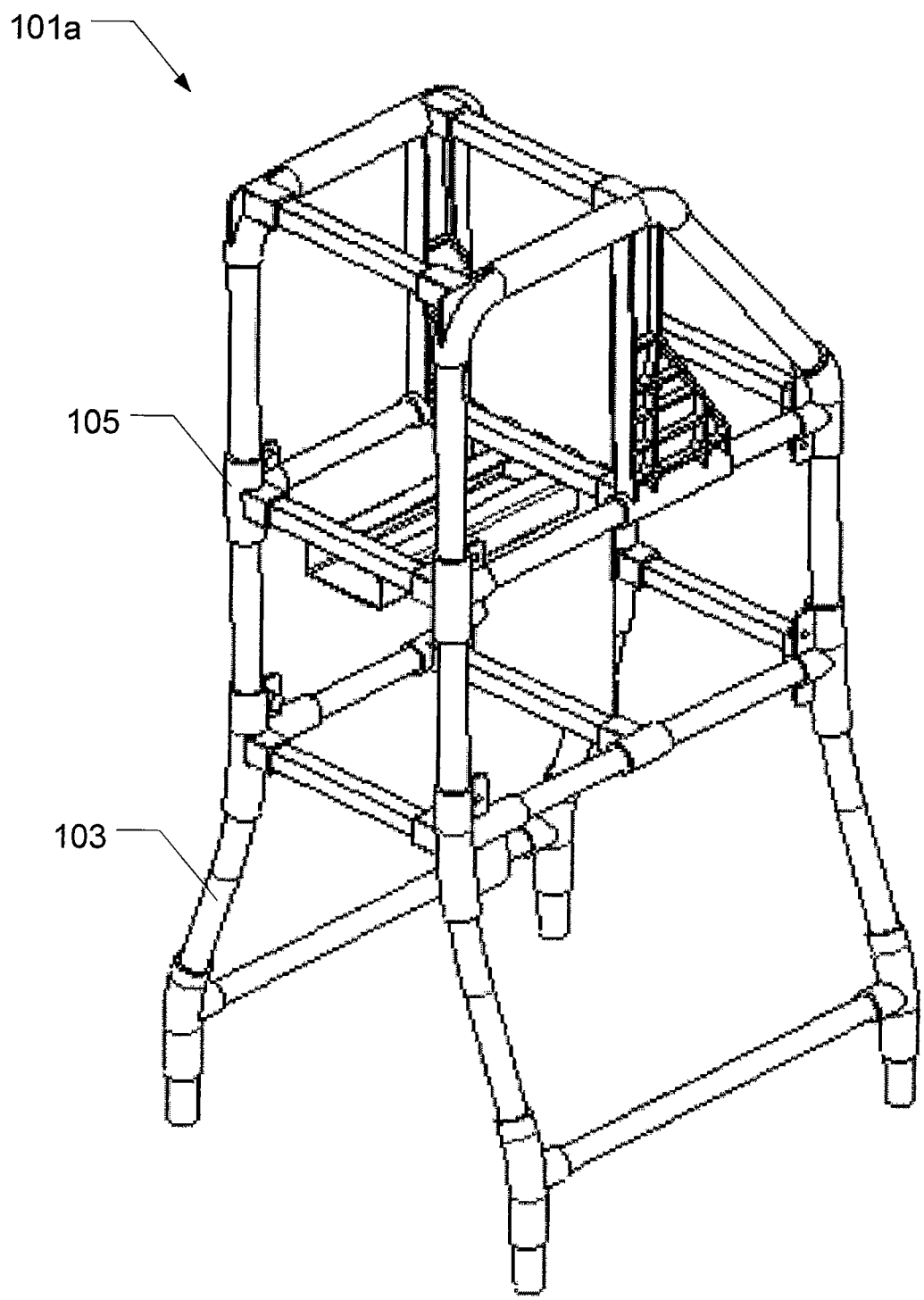
FIGS. 1a-b illustrate a rod structure of a structural frame system, according to two embodiments.
Figure 1B:
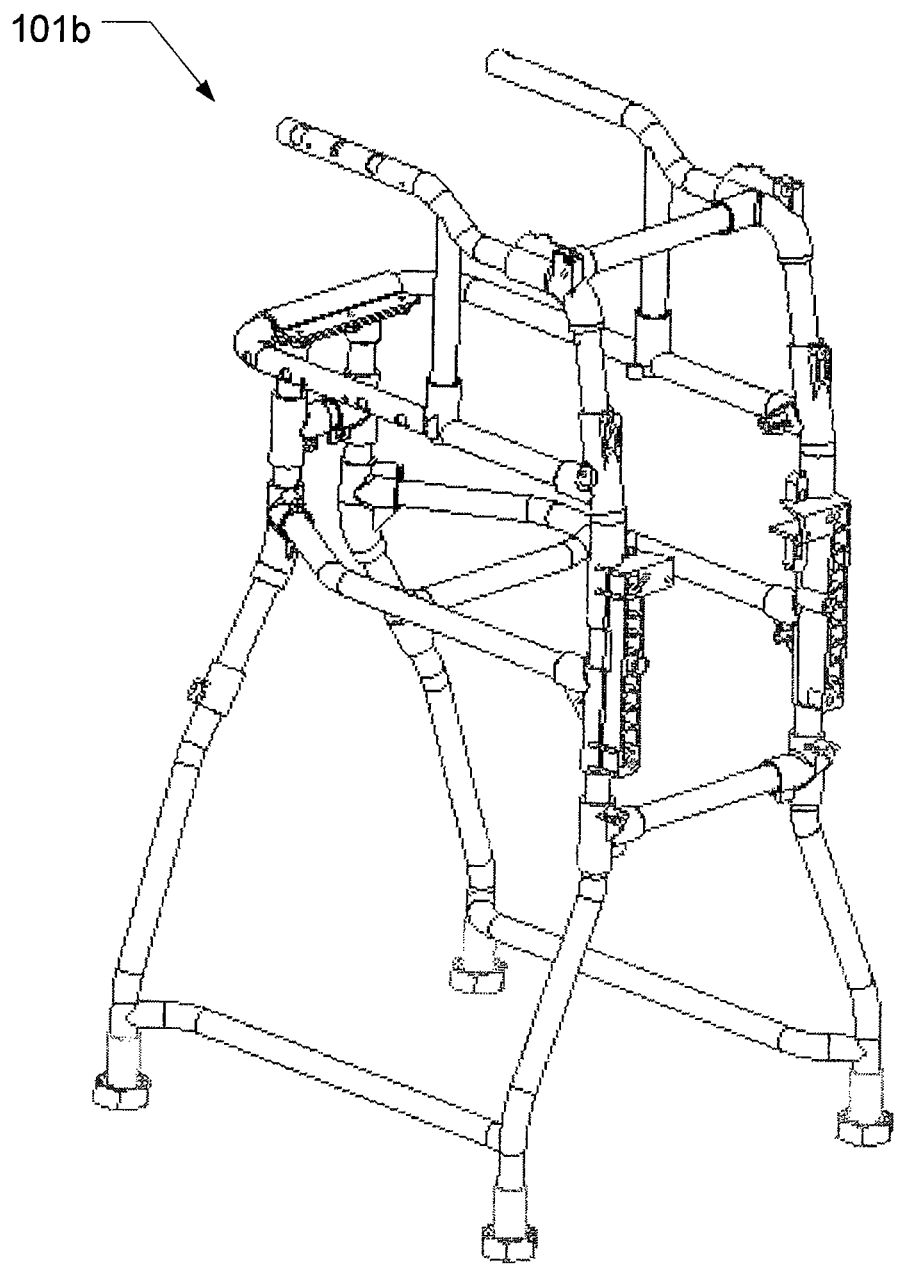
Figure 2:
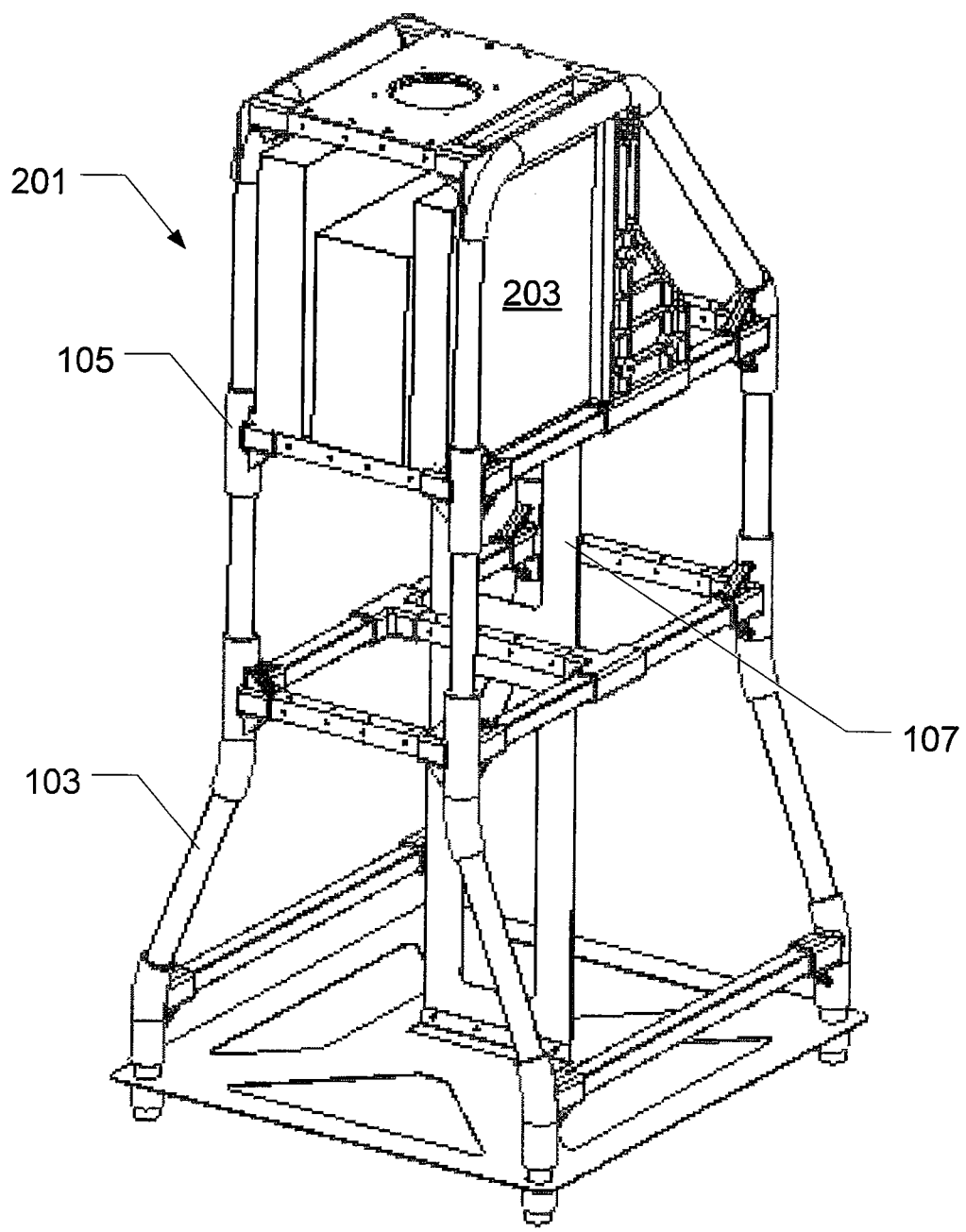
FIG. 2 illustrates a surgical system with an incorporated structural frame system, according to an embodiment.
Figure 3:
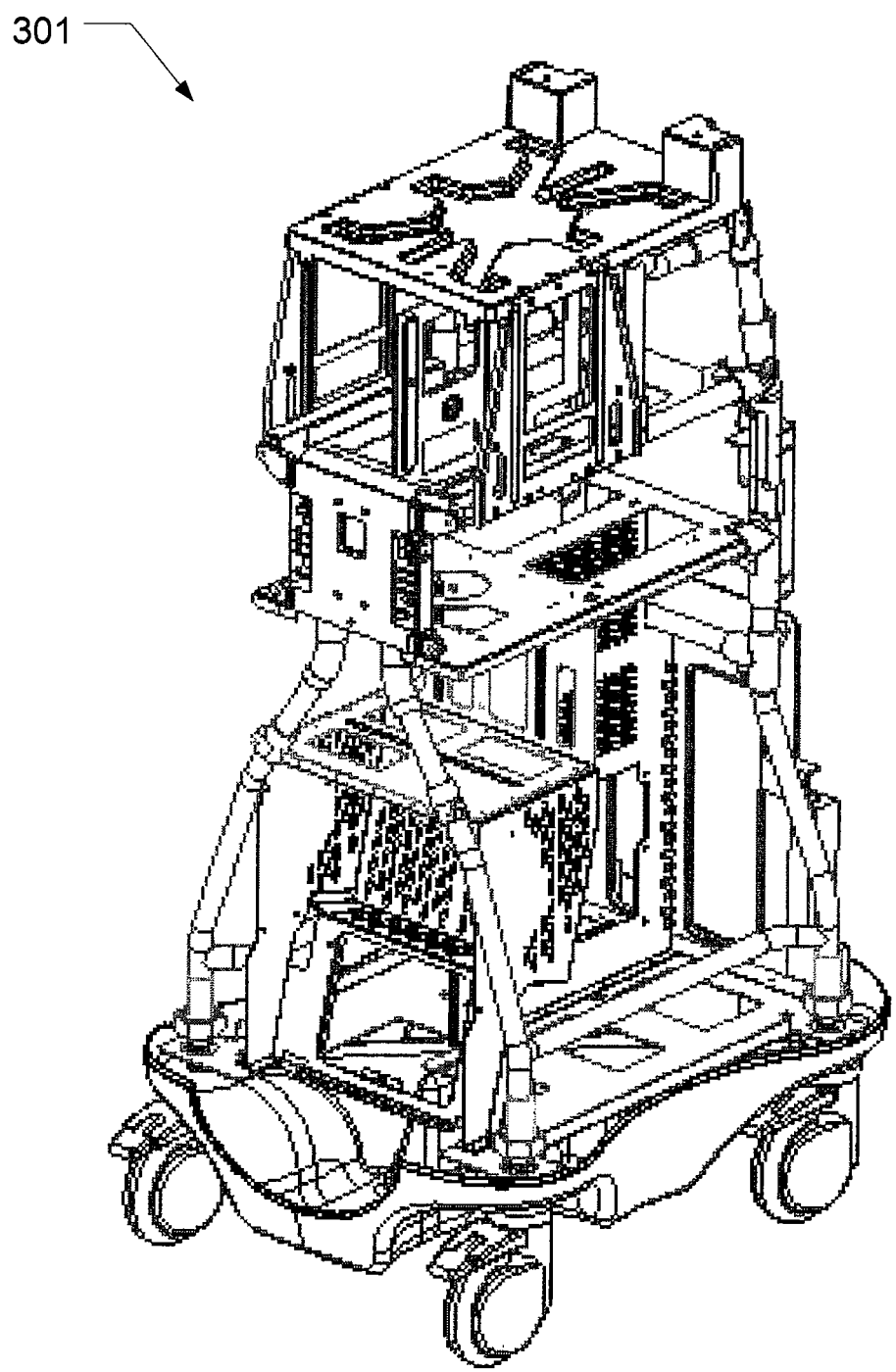
FIG. 3 illustrates a surgical system with an incorporated structural frame system, according to another embodiment.
Figure 4A:
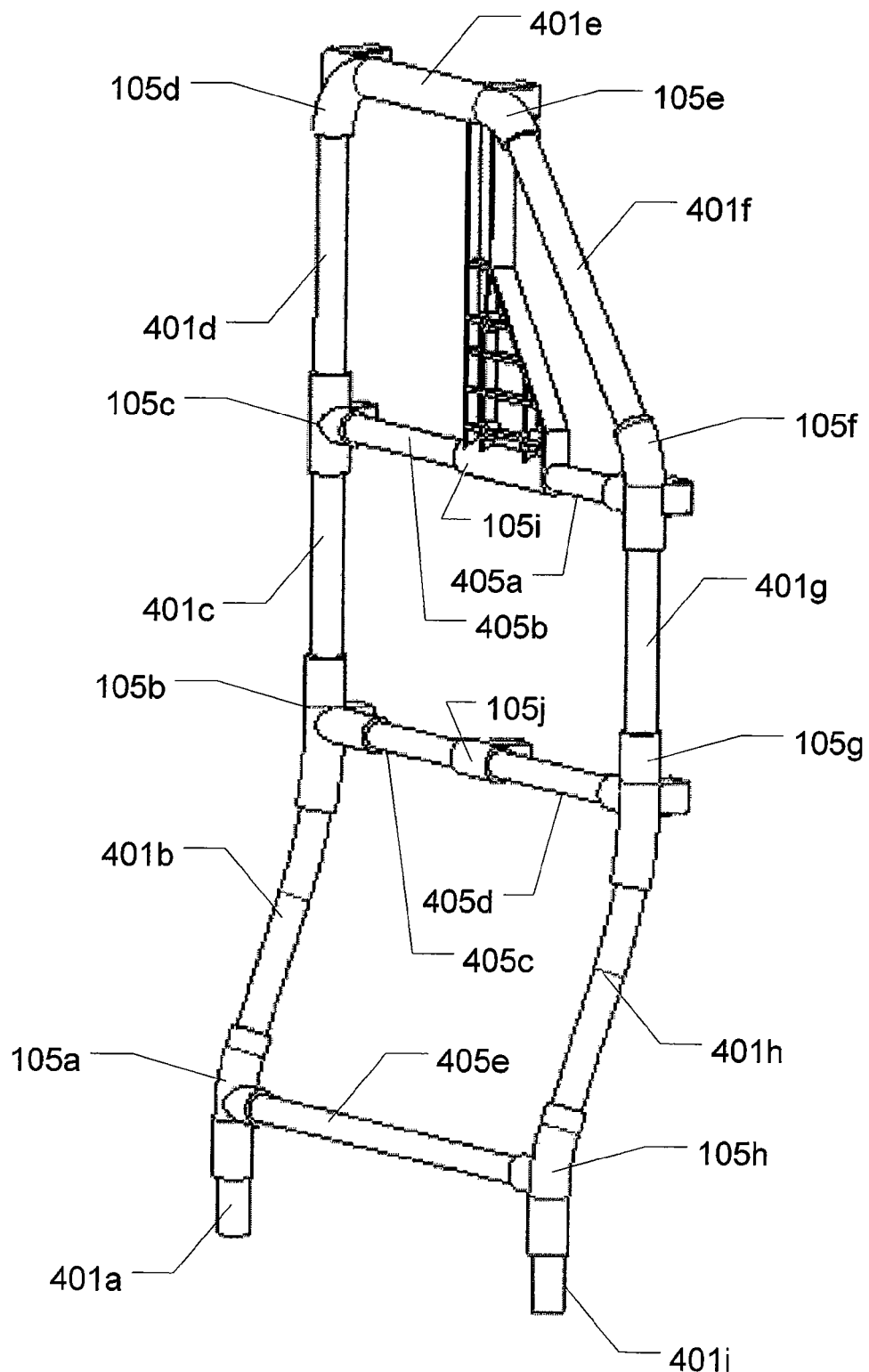
FIGS. 4a-b illustrate different views of a rod structure with incorporated interface joints, according to an embodiment.

FIGS. 1a-b illustrate embodiments of a structural frame system 101a-b (generally referred to herein as "frame system 101") that includes various interface joints 105 and structure members to support various loads throughout the frame system 101. In some embodiments, the components of a surgical system (e.g., an ophthalmic surgical system 201 (FIG. 2) or ophthalmic surgical system 301 (FIG. 3)) may be incorporated/coupled to the structure frame system 101. In some embodiments, interface joints 105 may be coupled to and/or molded over portions of a rod structure 103 to provide mounting points for structure members and other components. For example, rod structure 103 may include structural members 401a-i that are attached together through corresponding interface joints 105. As another example, as seen in FIG. 4a, structural members 401a-i may be part of a continuous rod (e.g., a rod bent to a predetermined shape) and the interface joints 105 may be molded (e.g., insert molded, injection molded, gas-assist injection molded, metal injection molded, Thixomolded, compression molded, hand layup, cast molded, etc.) over the continuous rod to provide mounting points for structure members and other components. Other techniques for forming the rod structure 103, structural members, etc. are also contemplated. For example, the various components may be machined, welded, pultruded, extruded, hand layup, or hydroformed.

As seen in FIG. 4a, in some embodiments, cross-face structural members 405a-e may be attached to various respective interface joints 105a-h (generally referred to herein as "interface joint 105") by overmolding the interface joint on the rod structure 103 and the cross-face structural members 405a-e. In some embodiments, the cross-face structural members 405a-e may be attached by sliding the cross-face structural members 405a-e into receiving holes in previously formed interface joints 105. As shown in FIG. 4a, cross-face structural members 405a and 405b may form a continuous cross-face structural member (both part of a single member that is similar to cross-face structural member 405e) that includes an interface joint 105i formed on the cross structural member. Similarly, cross-face structural members 405c and 405d may form a continuous cross-face structural member that includes an interface joint 105j formed (e.g., molded) on the cross structural member.

In some embodiments, material fillers such as carbon or glass fibers utilized for the interface joints 105 may be added during an initial compounding of a resin into a pellet for molding the interface joints 105. In some embodiments, a twin screw extruder may be used to create the pellets and appropriately blend in the material fillers. The pellets may then feed into a hopper of an injection molding machine and drawn into the molded machine's heated barrel and screw where the pellets may be melted and then shot into a tool to create a desired interface joint (e.g., around a section of the rod structure 103). During the insert molding process, a portion of the frame's system (e.g., a portion of the rod structure, structural members, etc.) may be placed into an injection molding machine's tool (e.g., see mold halves 903a,b shown in FIG. 9b). The tool may be closed and shut off around the portion in specific regions to shut off where the plastic is to flow to form the interface joint geometry around the inserted portion. Other molding processes are also contemplated.

Figure 4B:
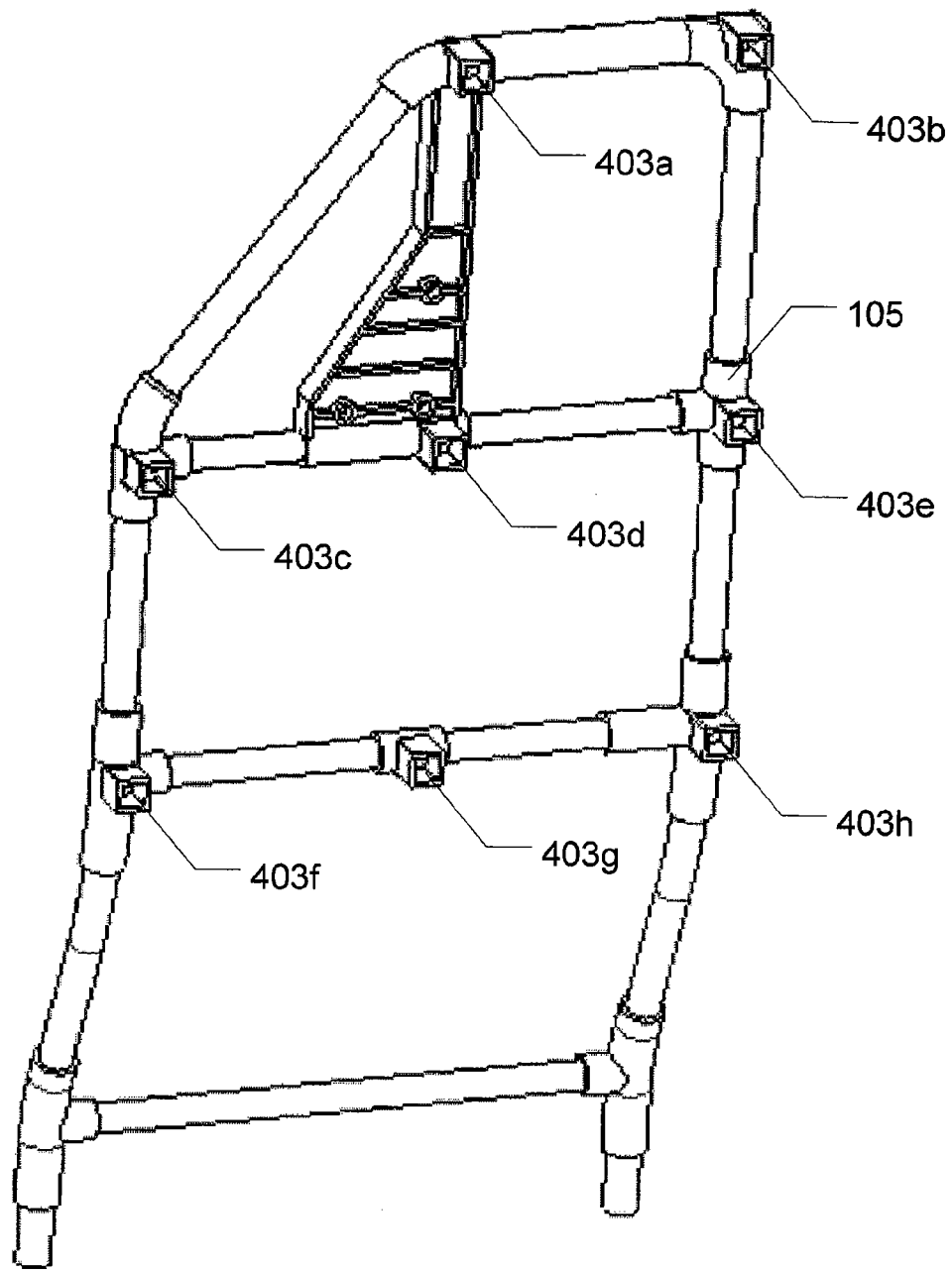
Figure 6:
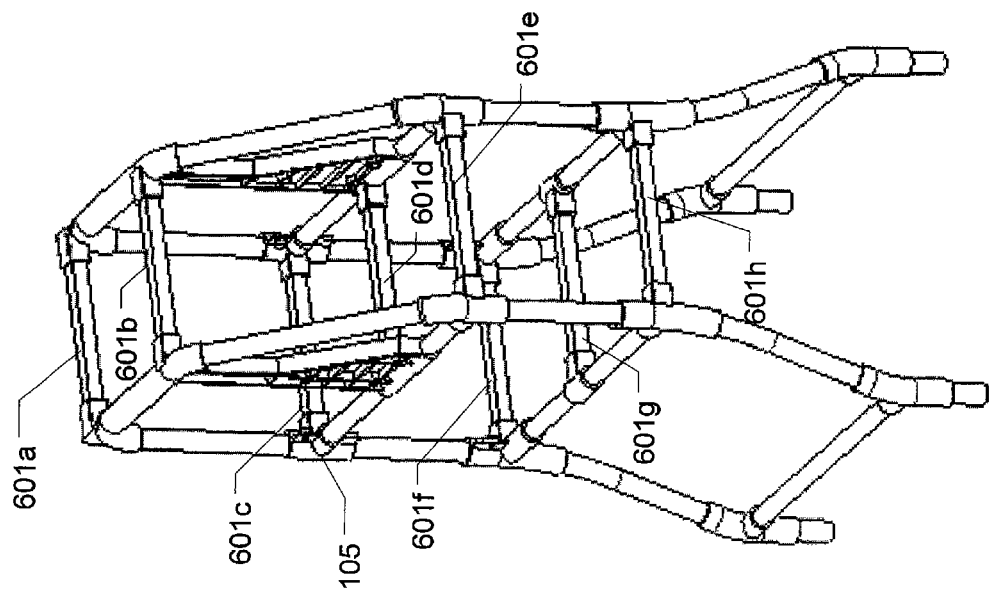
FIG. 6 illustrates two rod structures coupled together through cross-structural members, according to an embodiment.
Figure 5:
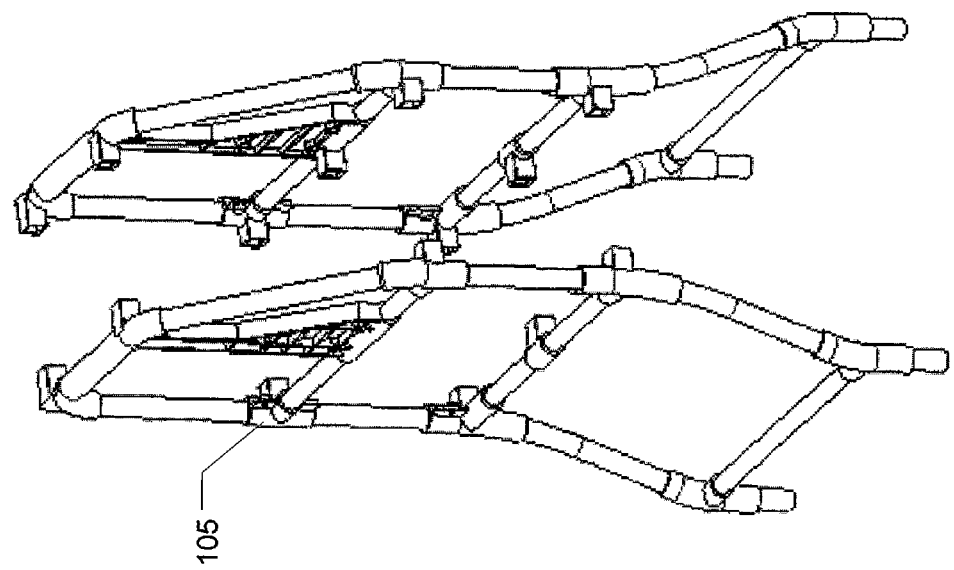
FIG. 5 illustrates two rod structures prior to attachment, according to an embodiment.
Figure 7:
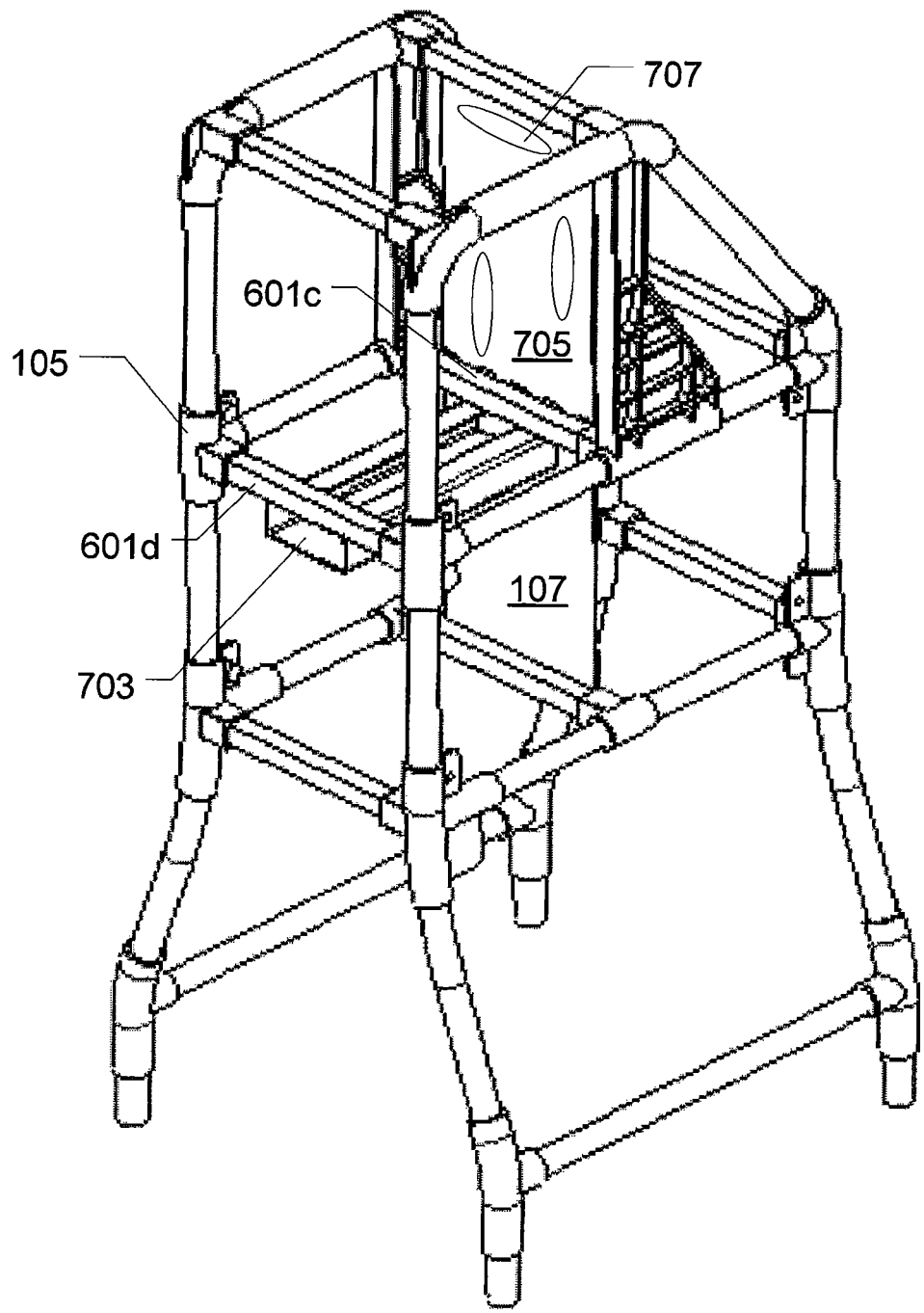
FIG. 7 illustrates various components attached to the frame system, according to an embodiment.

As seen in FIG. 4b, the interface joints 105 may include receiving holes 403a-h for cross-structural members to connect rod structure 103 with another rod structure. For example, FIG. 5 shows two rod structures 103 prior to connecting and FIG. 6 shows the two rod structures connected through cross-structural members 601a-h that interface with the rod structures 103 through the interface joints 105. As seen in FIG. 7, additional structures and components can be attached to the interface joints 105, rod structures 103, and/or cross-structural members 601a-h. For example, aesthetic skins 107 (also seen in FIG. 2) may be attached (e.g., snapped, glued, ultrasonically welded, swaged, or fastened) to the composite rod structure 103. As another example, tray mounting point 703 may be attached to the composite rod structure 103 (e.g., through attachments to cross-structural members 601c-d). As a yet further example, a printed circuit board 705 may be attached and may include interface connectors 707 for interfacing with a surgical module (e.g., module 203 which may be slid into the frame system 101).

FIGS. 8a-d illustrate various embodiments of an interface joint 105. The interface joint 105 shown in FIG. 8a may be overmolded on rod sections 401c-d (which may form a continuous rod through the overmolded interface joint 105) and rod section 405a to attach rod sections 401c-d to rod section 405a and provide an attachment point (such as a receiving hole 403e to receive structural member 601c). In some embodiments, an adhesive may be applied to the interior of receiving hole 403e and/or structural member 601c prior to insertion of structural member 601c into receiving hole 403e. The adhesive (e.g., glue or epoxy) may include 3M ADH 2216 B/A Epoxy, JD Lincoln 2-part high peel paste-PART (oxirane, 2,2-{methylenebis (phenleneoxymethylene)) bis-reaction product of epichlorohydrin and bisphenol A 40-60%, polymer/solids <8%, benezenediol <2%, silica-amorphous-fumed <7% and fibrous glass <2%) and PART B (Poly(oxy (methyl-1,2-ethanediyl)), alpha-2-amino-methyleneyl) omega-2-aminomethylethoxy) 25-45%, benzyl alcohol >10%, triethylenetetramine <2%, nonyphenol <5%, silica-amorphous, fumed 5-25%, polyamine <30%, tertiary amine <5% and cycloaliphatic amine <15% and Hendel Loctite Speedbonder H4500 two part component room temperature curing 10:1 mix ration methacrylate adhesive system. Other adhesives are also contemplated.

Figure 8A:
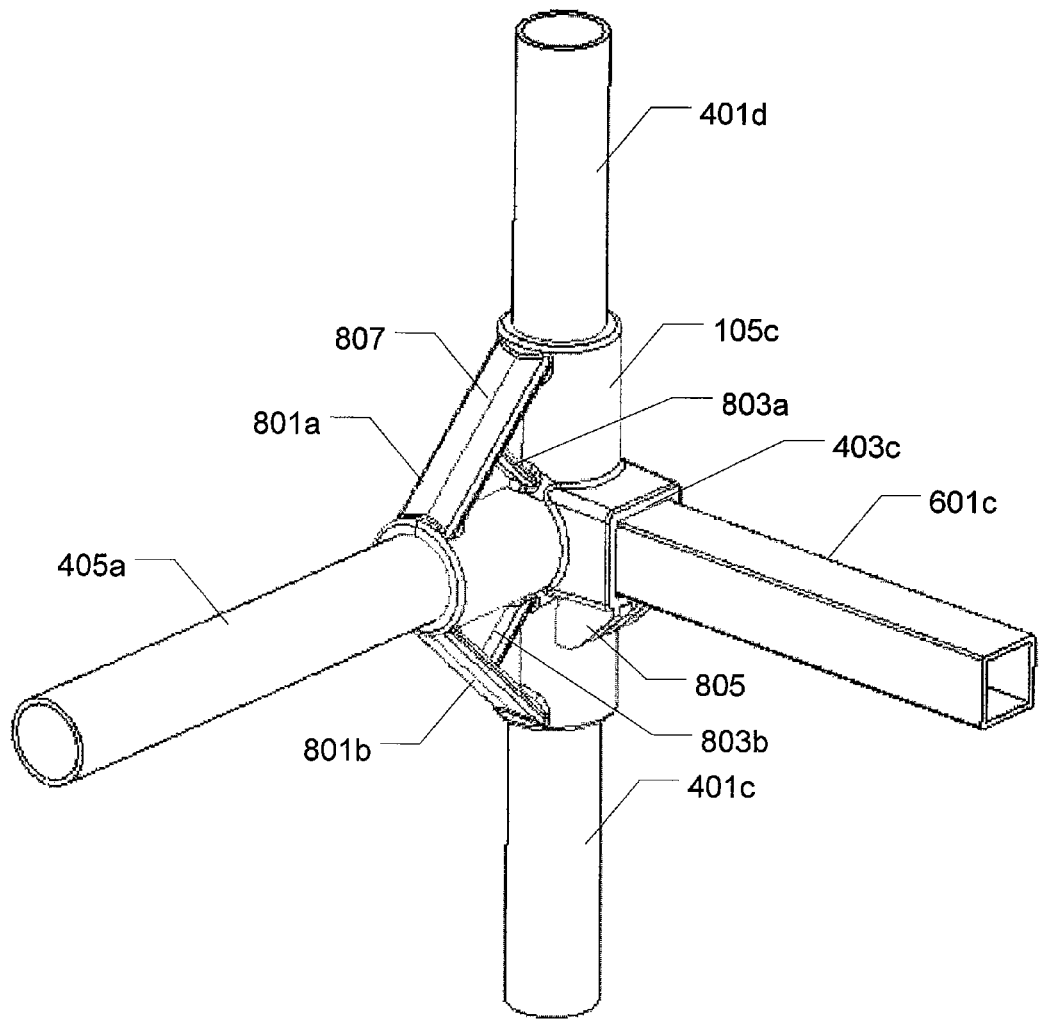
FIGS. 8a-d illustrate embodiments of various interface joints.
Figure 8B:
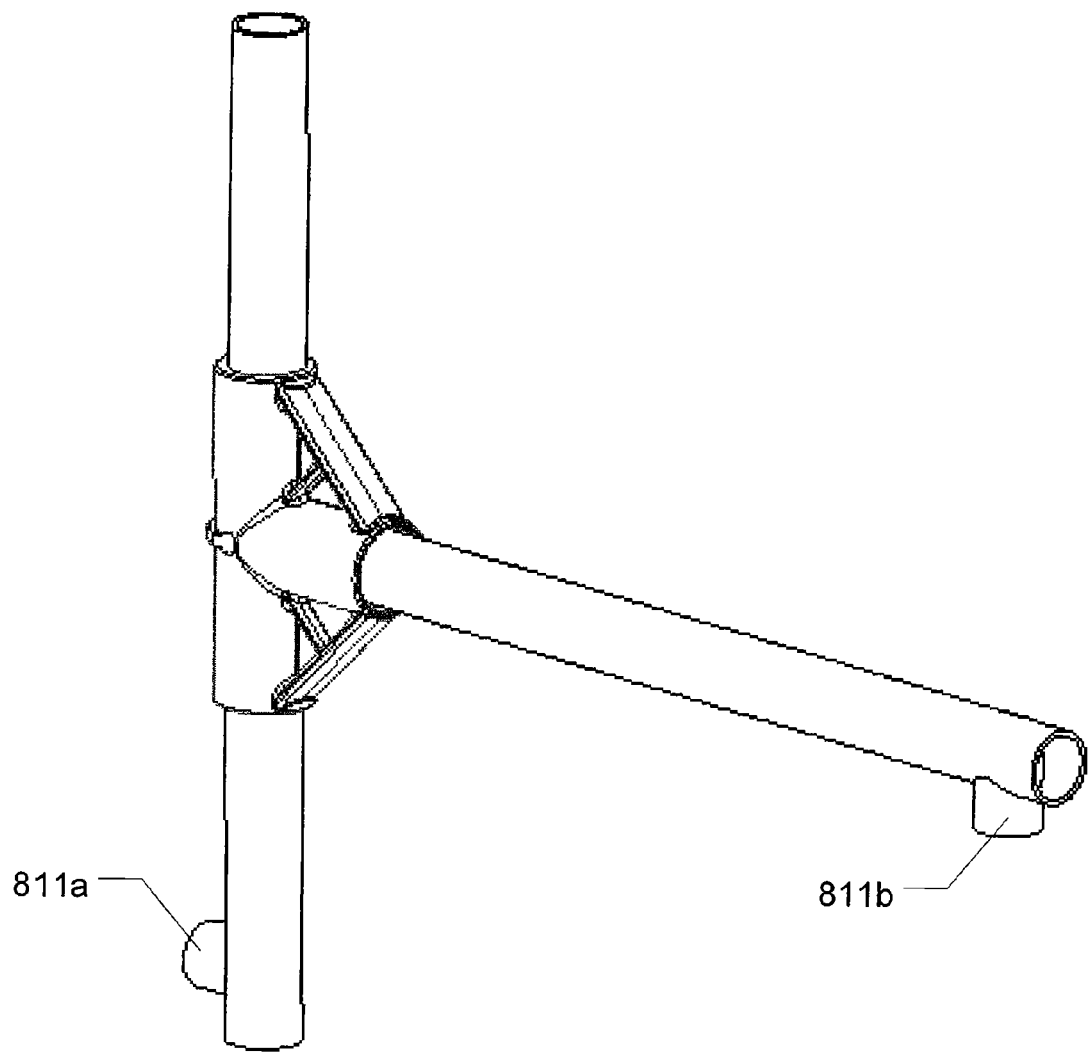
Figures 8C, 8D:
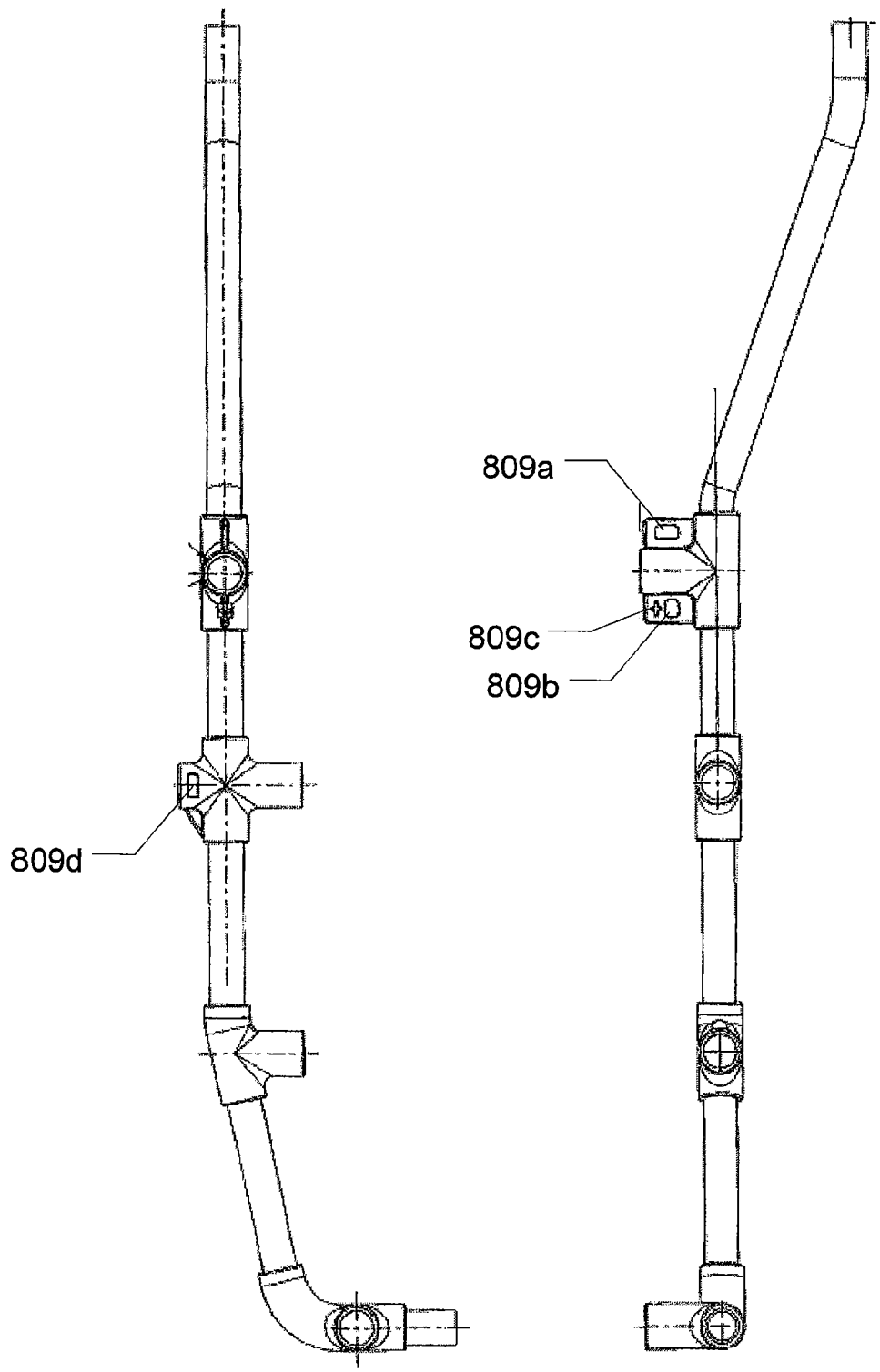

As also seen in FIG. 8a, interface joint 105 may include structural features such as braces 801a-b, braces 803a-b, and brace 805 to increase the strength of the interface joint 105. The various braces may be formed through the molding process or may be attached after the molding process. Also as seen in FIG. 8a, a mold seam line 807 may form where an upper mold and a lower mold meet (e.g., in a cast or injection molding process) to form the interface joint (e.g., the molds may meet with the rod sections 401c-d and 405a in between the molds prior to injecting, for example, a plastic in a space defined by the upper and lower molds). FIGS. 8b-d illustrate additional embodiments of rod structures 103 and interface joints 105. As seen in FIG. 8b, the rod structure may include one or more mounting points 811a-b (which may include, for example, protrusions with holes extending into the interior of the rod structure). As seen in FIGS. 8c-d, interface joints may have one or more holes 809a-d for receiving and/or attaching components in the frame system 101.

Figure 9A:
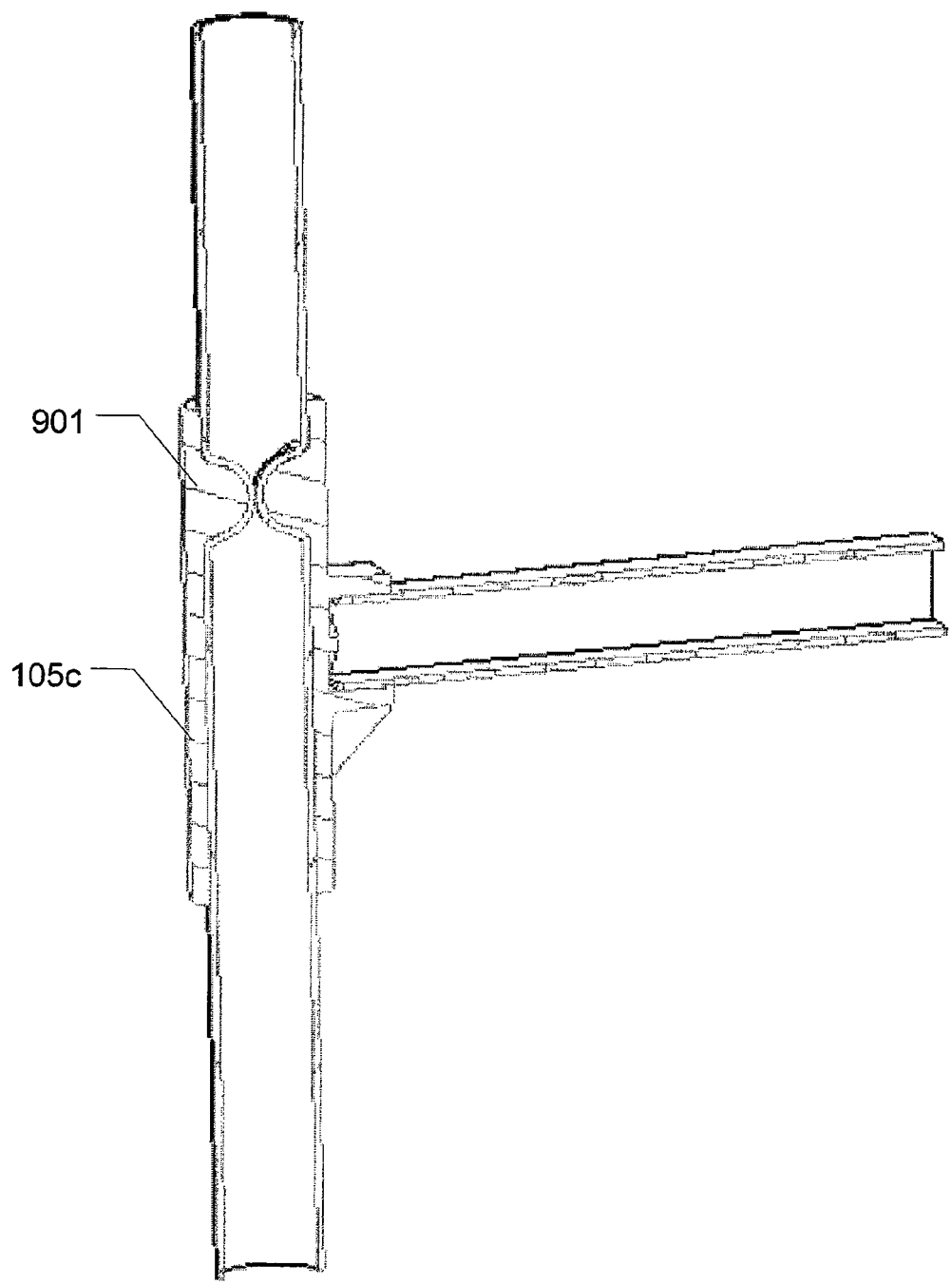
FIGS. 9a-b illustrate a cross-sectional view of an embodiment of an interface joint and molding tool.
Figure 9B:
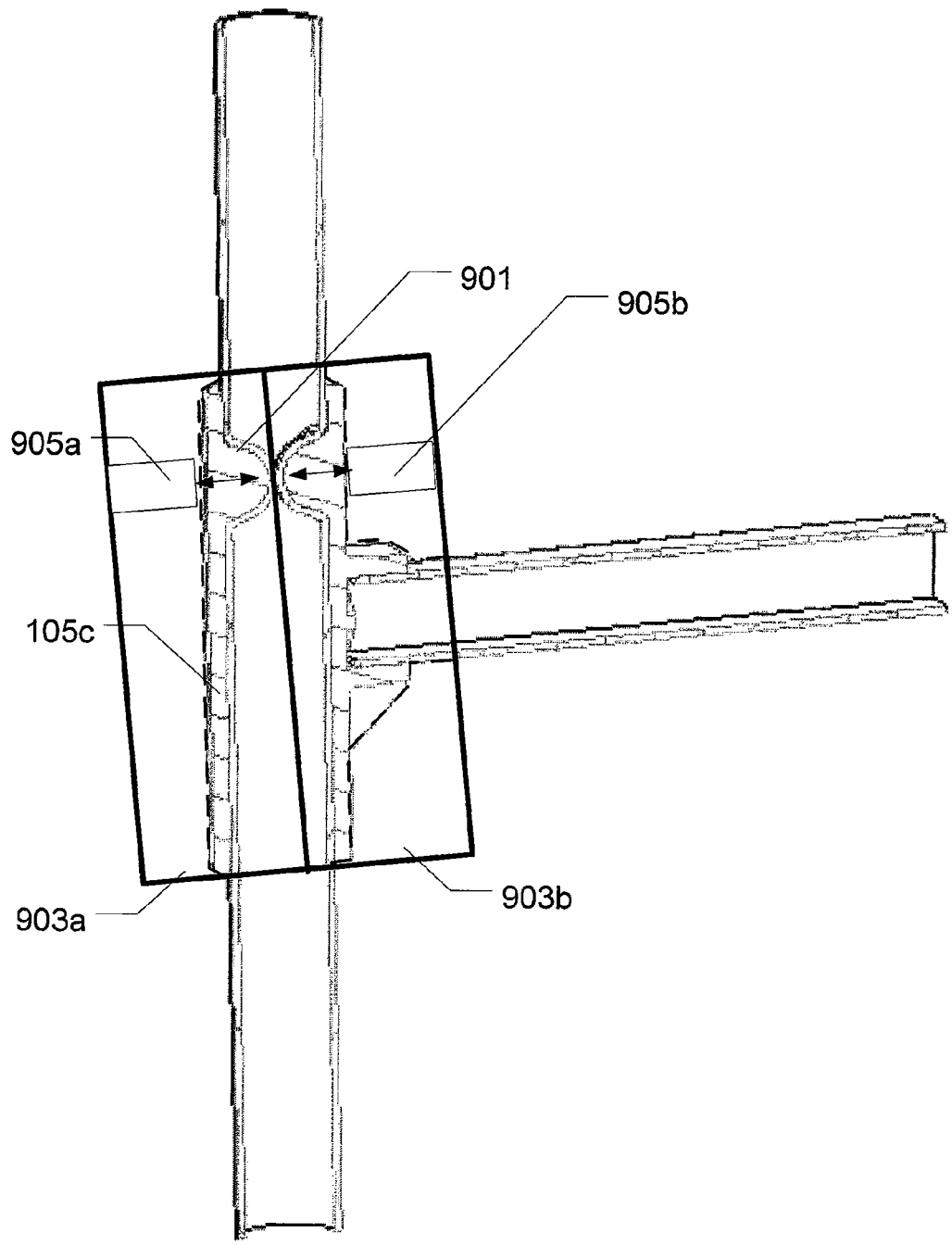

FIGS. 9a-b illustrates a cross section of an embodiment of an interface joint 105c that includes an attachment point 901. To secure the interface joint 105 to the rod structure 103, one or more attachment points 901 (e.g., an indentation or cutout) may be made in the rod structure 103 prior to or during the molding of the interface joint 105. The attachment points 901 may allow molding material from the interface joint 105 to collect into the attachment points 901 to hold the interface joint 105 in place (i.e., to prevent the interface joint 105 from slipping and/or impede creepage along the rod structure 103). For example, the attachment point 901 may include an indentation made in the rod structure 103 (e.g., by pressing a feature into the surface of the rod structure 103 to form a dimple in the rod structure 103) that allows molding material to collect in a depression of the indentation. As another example, the attachment points 901 may include cutouts (e.g., stamped through the rod structure) that allow molding material to enter an interior of the rod structure 103. In some embodiments, attachment points 901 may not be used (e.g., adhesive may be used to secure the interface joints 105 to the rod structure 103).

Figure 10A:
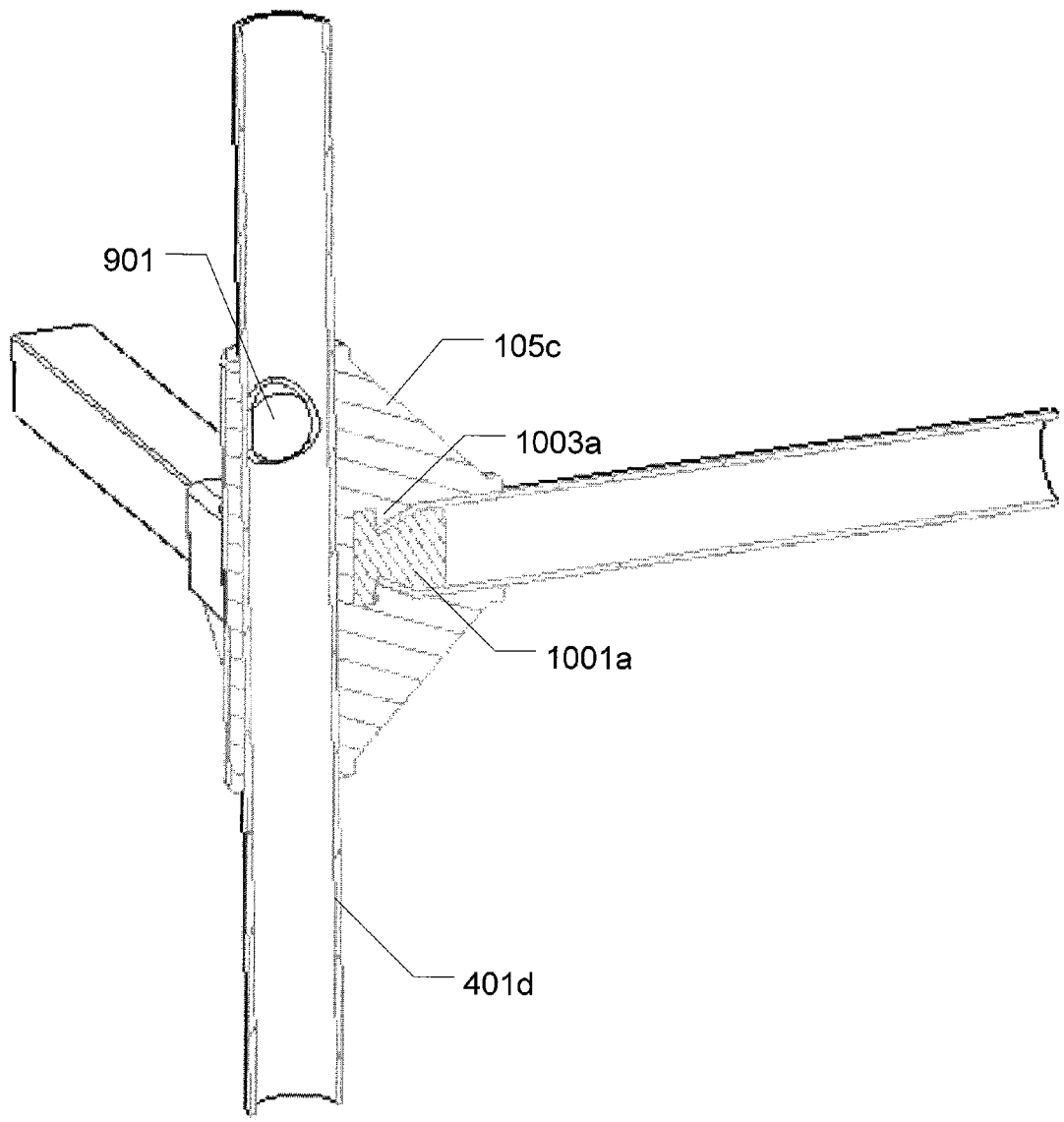
FIG. 10a-b illustrate cross-sectional views of two embodiments of an interface joint and a structural member with a plug.
Figure 10B:
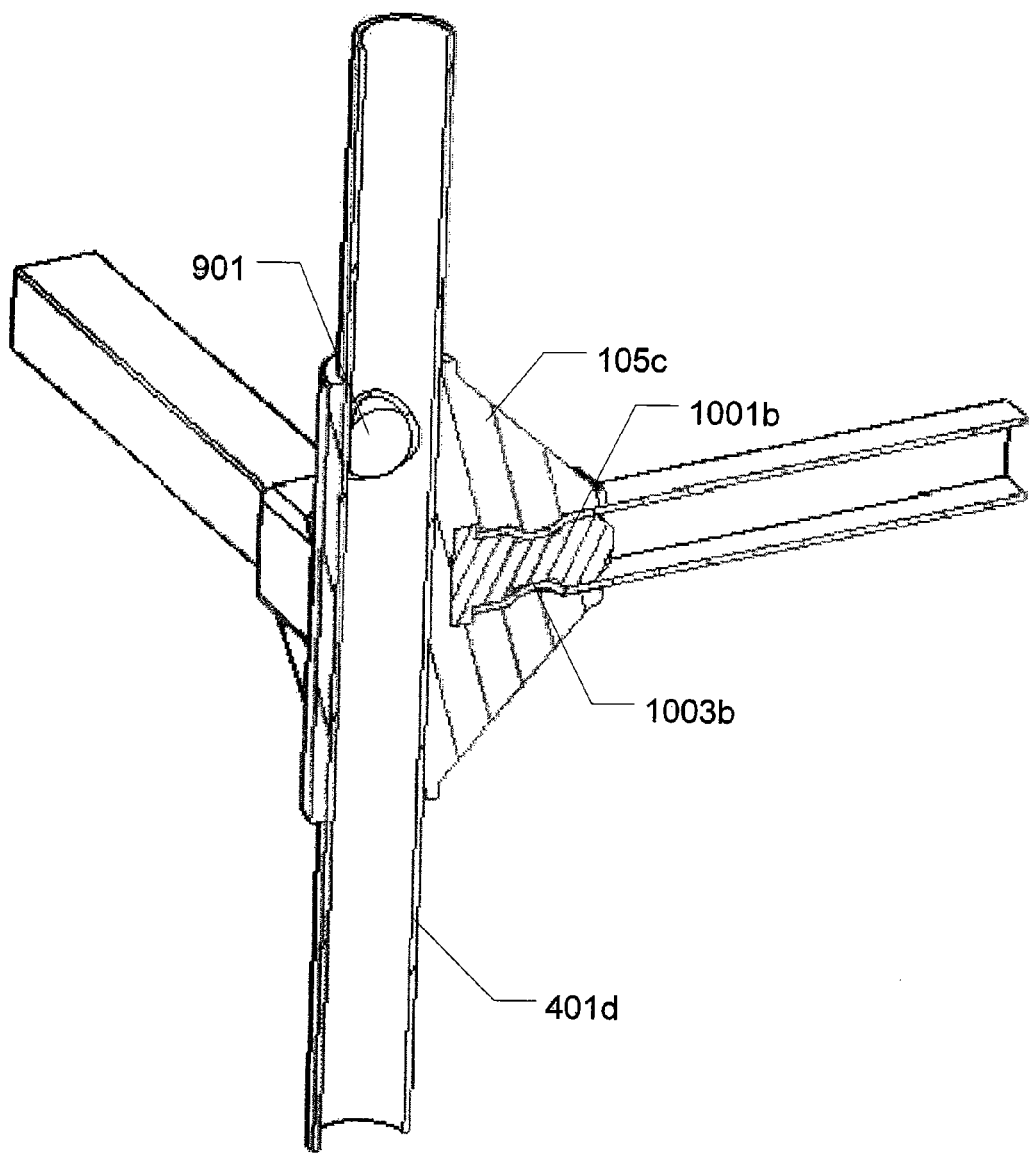
Figure 11:
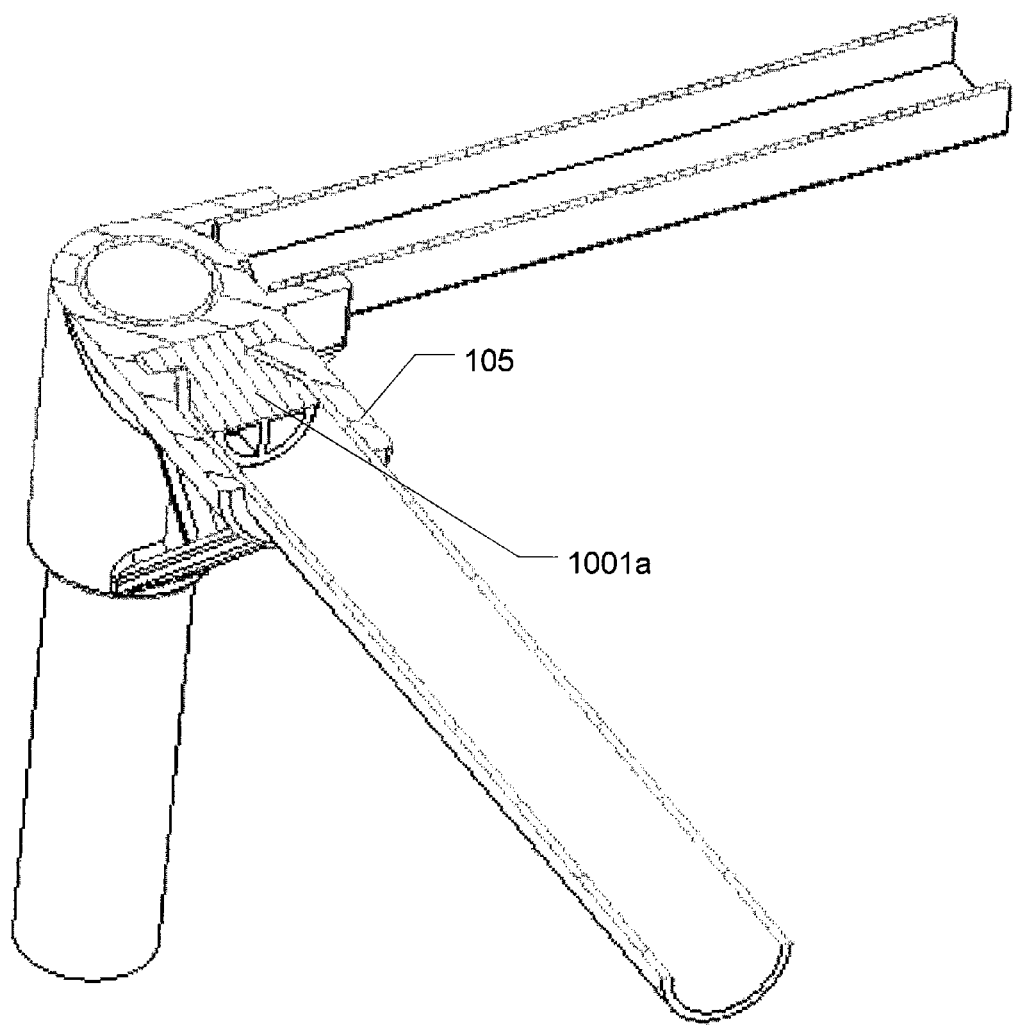
FIG. 11 illustrates another cross-sectional view of an interface joint and a structural member with a plug, according to an embodiment.

FIGS. 10a-11 illustrate cut-away views of various interface joints 105. In some embodiments, the structure members coupled to interface joints 105 may include a plug (e.g., plug 1001a/b). As seen in FIG. 11, the plug 1001a may be formed on an end of the structure member (e.g., structural members 401a-i, structural members 405a-e, cross-structural members 601a-h, etc.) to inhibit flow of molding material from the interface joint 105 into an interior of the structure member. FIG. 10a illustrates a cut-away section of a plug 1001a for a round structural member and FIG. 10b illustrates a cut-away section of a plug 1001b for a square structural member. In some embodiments, the structure member may include a crimped section (e.g., crimp 1003a/b) with a reduced diameter to secure the plug 1001 in place. The plug 1001 may be formed separately from the structure member and inserted into the structure member (after which the structure member may be crimped to hold the plug) or the plug 1001 may be formed directly on the end of the structure member (e.g., molded onto the end of the structure member by inserting the end of the structure member into a plastic mold).

Figure 12A:
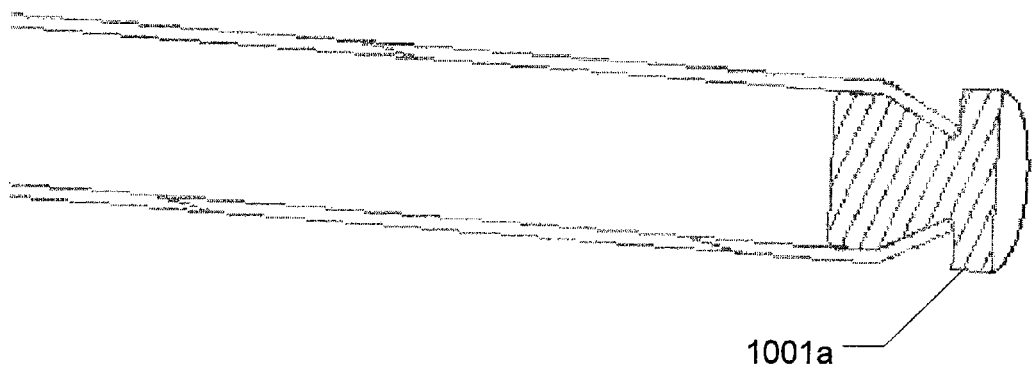
FIGS. 12a-b illustrate two views of a plug for a structural member, according to an embodiment.
Figure 12B:
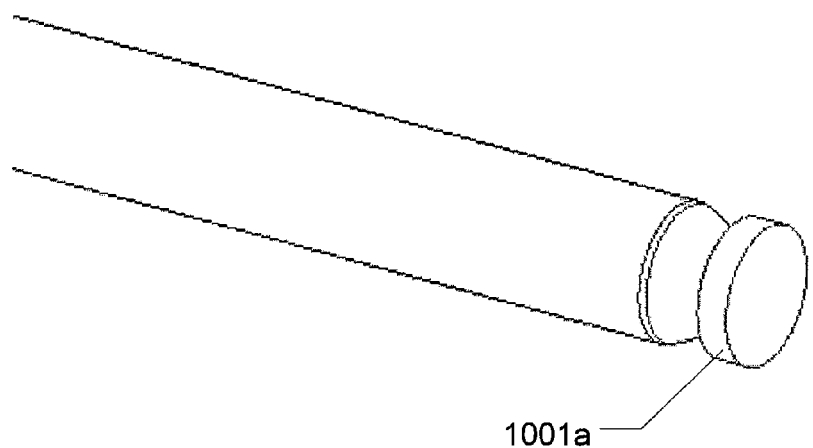

In some embodiments, the plug 1001a/b may be made of a material with an equal or higher melting temperature (e.g., aluminum) than the material used to form the interface joint 105 (e.g., plastic) to prevent melting of the plug 1001a/b during the molding of the interface joint 105 over the plug 1001. FIGS. 12a-b illustrate views of the plugged structure member outside of an interface joint 105. In some embodiments, a plug 1001a/b may not be used (e.g., the end of the structure member may be left open and may receive some molding material during the molding of the interface joints 105 on the rod structure 103). In some embodiments, the plug 1001a/b may prevent molded material from entering crossface structural member 405a and may provide a small undercut to inhibit pull out of structural member 405a once structural member 405a is overmolded. In some embodiments, a flat corresponding geometrical shape may be welded to the end of member 405a in order to cap the end. In addition, plug 1001a may be made to contact member 103 to provide an electrical connection between members 405a and 103.

Figure 19A:
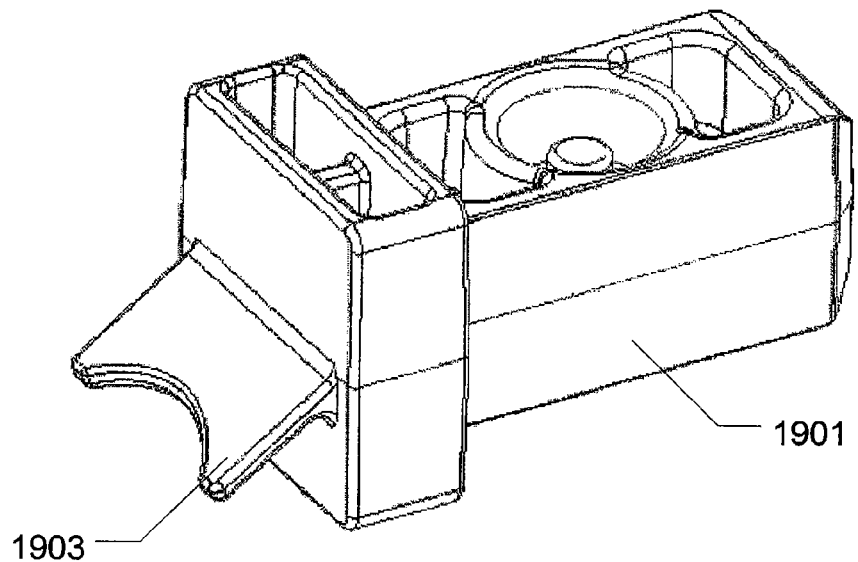
FIGS. 19a-g illustrate embodiments of a self centering plug.
Figure 19B:
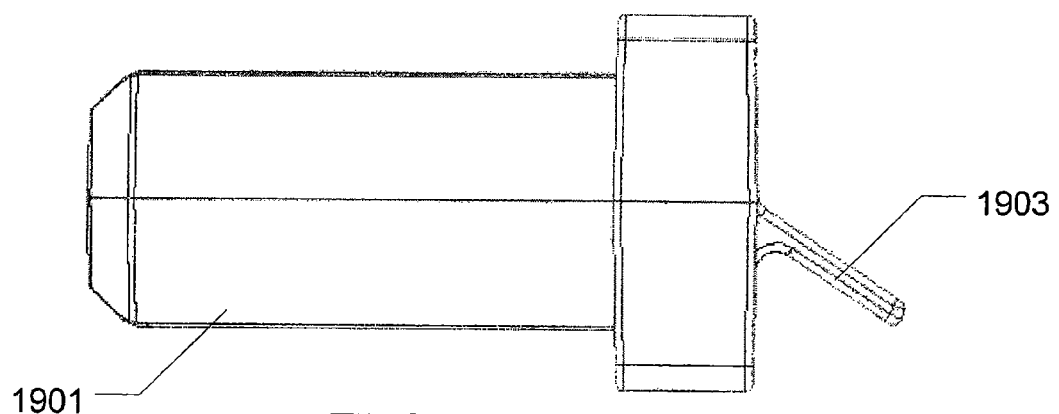
Figure 19D:
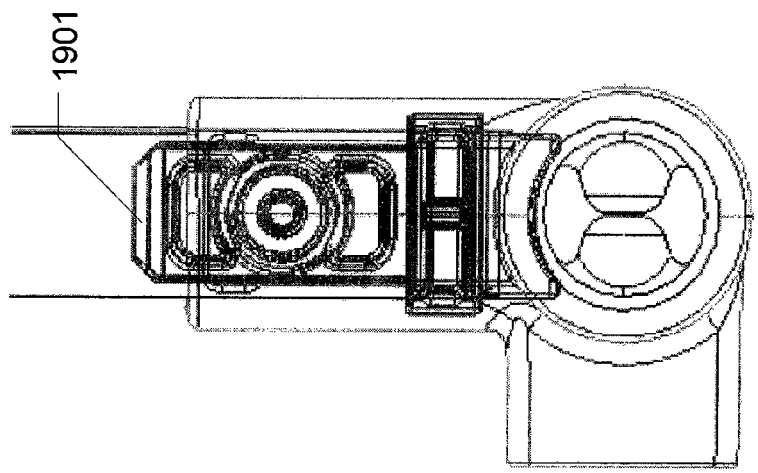
Figure 19C:
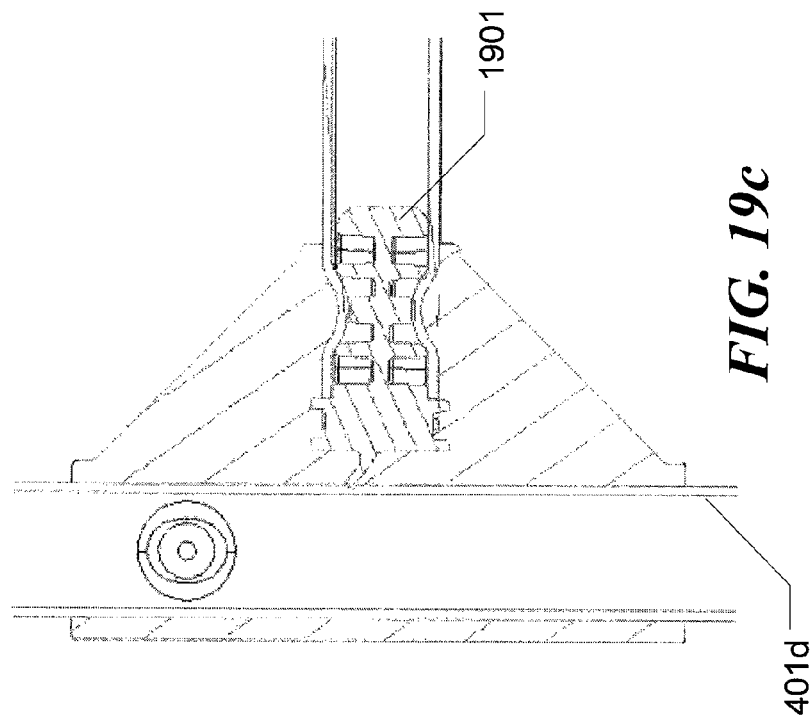
Figure 19E:
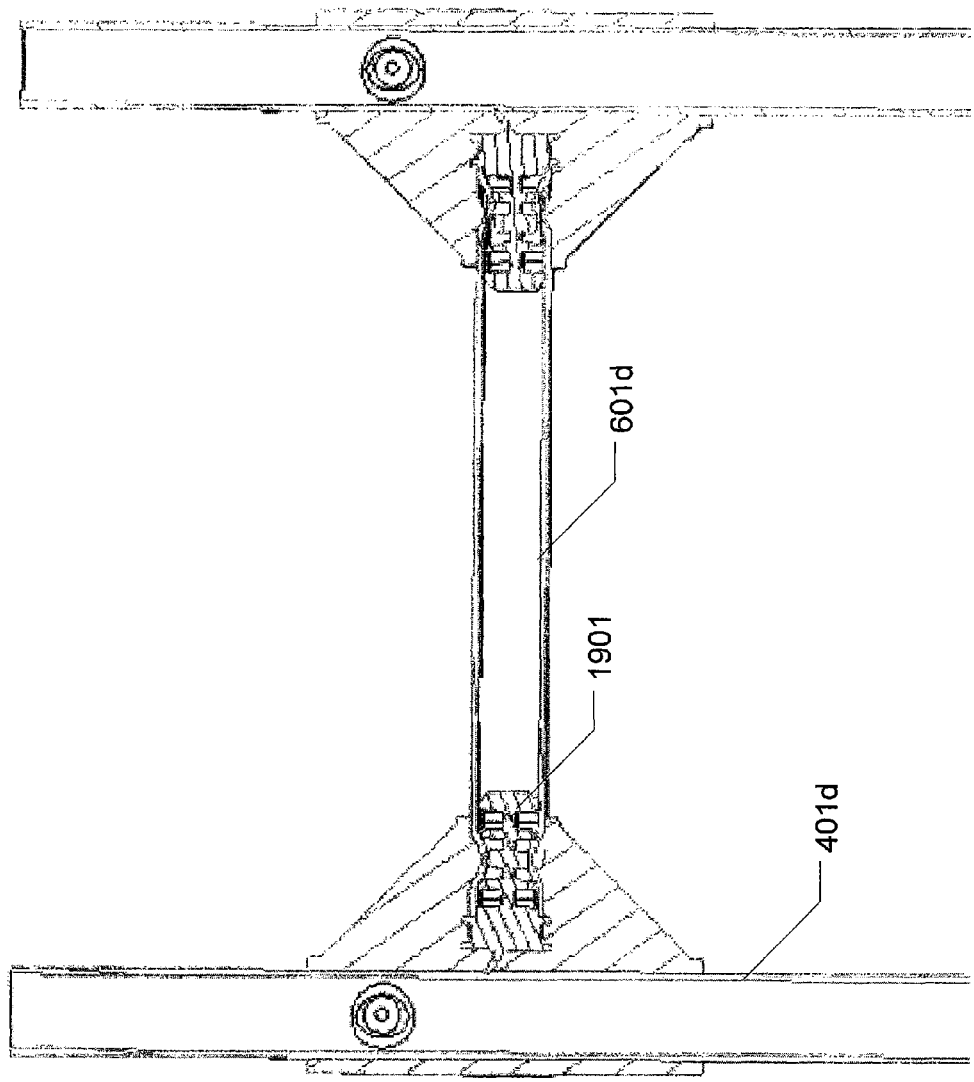
Figure 19F:
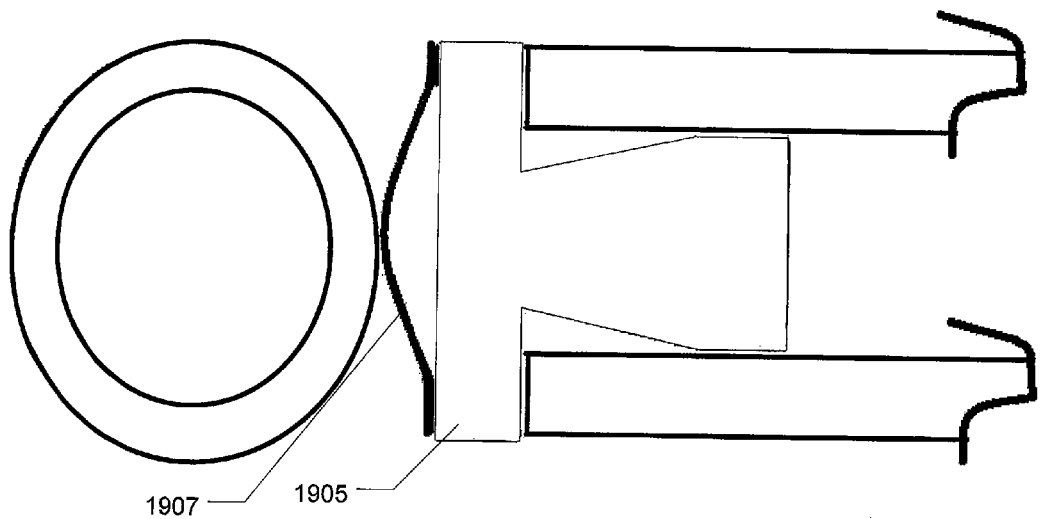
Figure 19G:
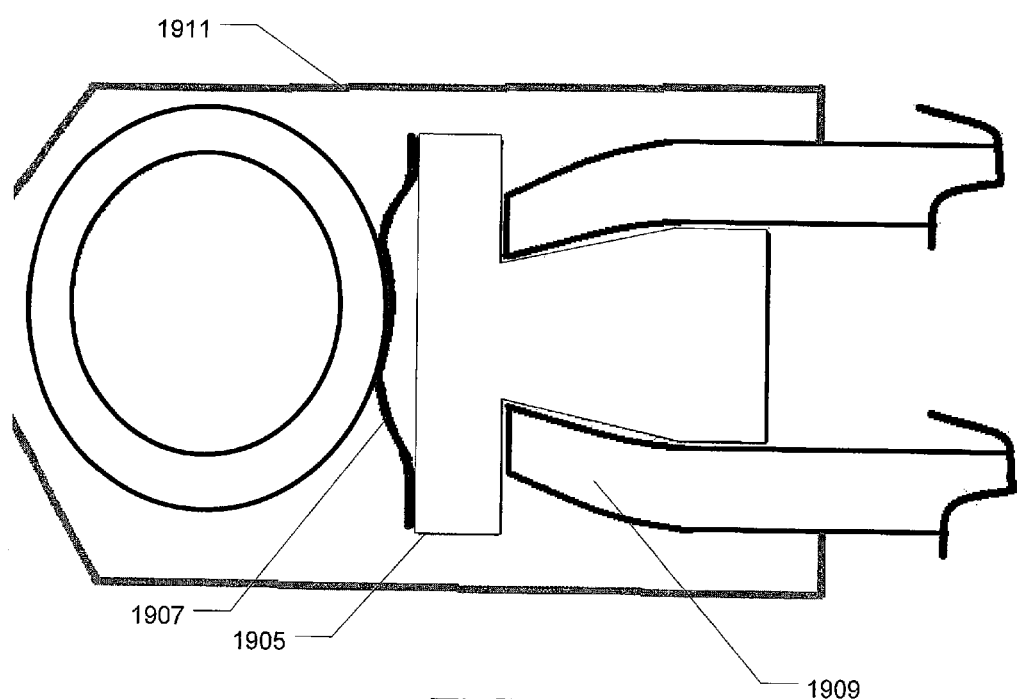

As seen in FIGS. 19a-e, an embodiment of the plug may include plug 1901 that may be configured to automatically center itself between members 103 on each side due to a molded in spring feature 1903 which may improve the reproducibility and repeatability of the assembly. The spring feature 1903 may include an angle and be flexible such that the spring feature 1903 may bend to allow movement of the plug 1901. The spring feature 1903 may further include a curve to abut against the outer curve of the structural member 401d (as seen in FIG. 19c). FIG. 19d illustrates the plug 1901 in a corner joint. FIG. 19e illustrates two plugs 1901 on either side of a structural member 601d. In some embodiments, the curve in the spring feature of each plug may allow the structural member 601d to center itself (via interaction between the curve and the outer profile of the outer structural member) between the outer structural members (e.g., 401d) prior to molding the interface joints 105. The spring on each side may act to center the rod since each spring should be displaced by approximately the same length (if each spring has approximately the same spring rate). In some embodiments, a hole or alignment feature may be used to center the tube structure in an injection molding tool to repeatably place the structure. This may result in a more repeatable pattern for fastening points on the cross member. FIGS. 19f-g illustrate another example of a spring connector. As seen in FIGS. 19f-g, connector 1905 may be coupled to a spring 1907 (e.g., a flexible wire structure) that may deflect (as seen in FIG. 19g) as the connector 1905 is pressed against a structural member. Connectors 1905 on each side of structural member 601 may center the structural member 601 as the structural member 601 is placed between outer structural members 401 (as an example) in a molding tool 1911. In some embodiments, the structural members 601 may be crimped 1909 around the connector 1905 (other coupling such as adhesive, snap fit, etc.) is also contemplated.

In some embodiments, a plug may not be used (e.g., as seen in FIG. 9a, the structure member may be, for example, attached to the interface joint 105c through an adhesive, friction fit, etc).

FIGS. 13a-16h illustrate inserts, according to various embodiments. Floating inserts 1301, 1401, and 1601 may provide tolerance between a screw (or other fastener) and the insert (such as a brass insert) in an assembly (such as frame system 101) for attaching a skin (such as a sheetmetal skin). In some embodiments, the insert may be positioned in a polymeric portion (such as in hole 2071a in the joint shown in FIGS. 20a-b) of the frame system 101 or in a metal portion (such as in hole 2071b in the structural member shown in FIGS. 20a-b). The insert may include an inner shaped plug (e.g., plug 1319 and 1419) with a squared end (e.g., end 1303 or 1403) and a rounded end (e.g., end 1305 or 1405). In some embodiments, both ends may be rounded (e.g., end 1603 and 1605 as seen in FIG. 16a). In some embodiments, a flange 1407 may be formed between the two ends with a threaded section 1409 formed through the center. In some embodiments, the exterior (e.g., exterior 1311 and 1411) may include a pattern with flutes or grooves to allow a melted polymer to flow freely into the crevices when the insert is ultrasonically welded into a polymeric boss (which may be formed and/or include hole 2071a,b). Once the melted polymer in the boss re-solidifies it may form undercuts that may hold the insert in the boss and prevent the insert from being pulled out. In some embodiments, a clearance (e.g., clearance 1413) may allow a center axis of the threads to float in X, Y, and Z dimensions (e.g., see displacement in FIG. 14c). In some embodiments, an interface between insert portion 1415 (as seen in FIG. 14e) and inset portion 1417 (as seen in FIG. 15) may inhibit rotation of plug 1319/1419 when screwing a screw (or attaching a different fastener) into the plug 1319/1419 through an interference fit between the edge portion 1415 and inset portion 1417.

Figure 13B:
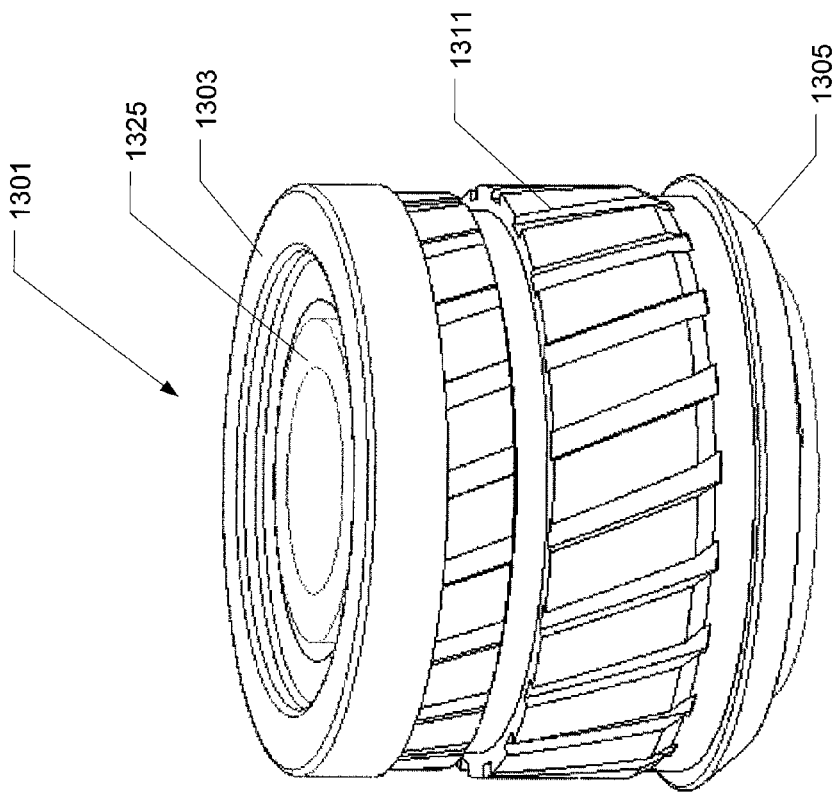
Figure 13A:
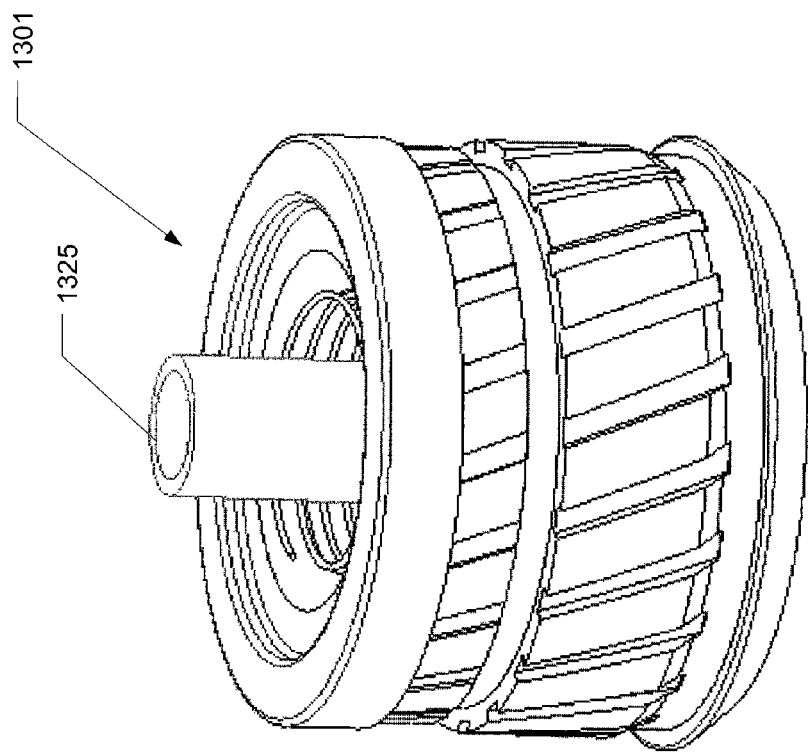
Figure 13D:
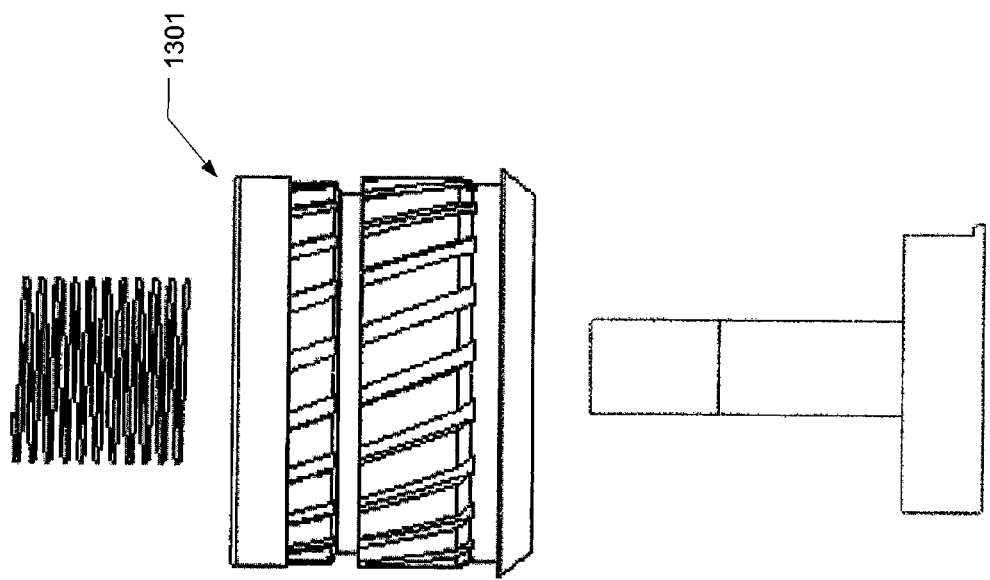
Figure 13C:
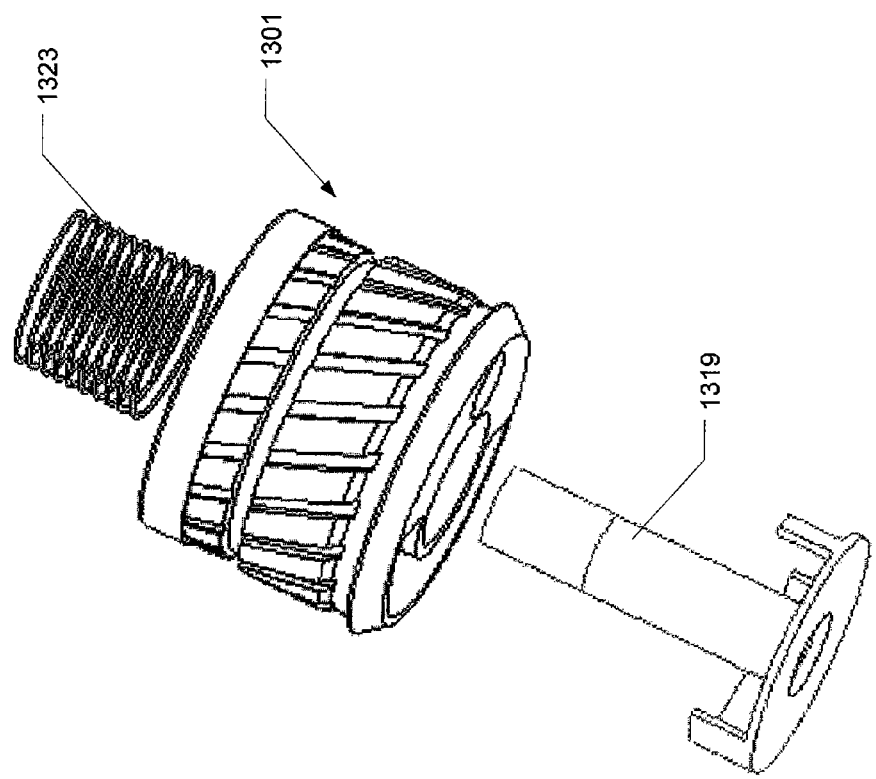
Figure 14C:
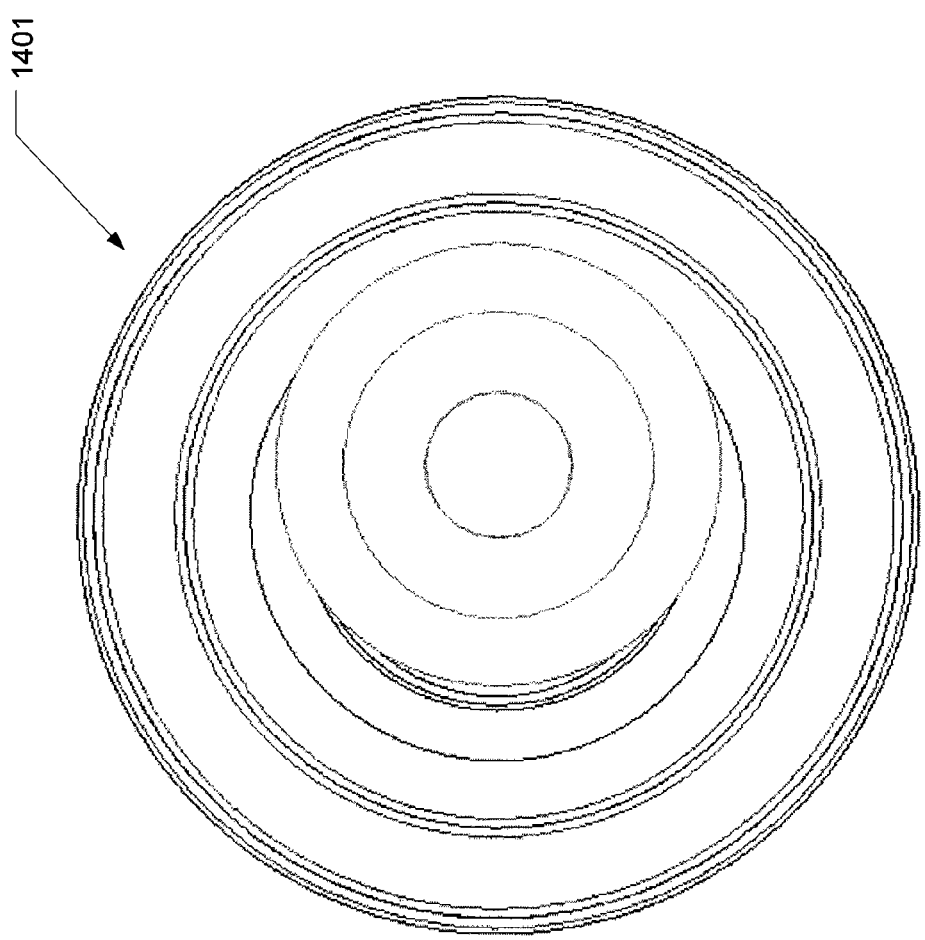
Figure 14D:
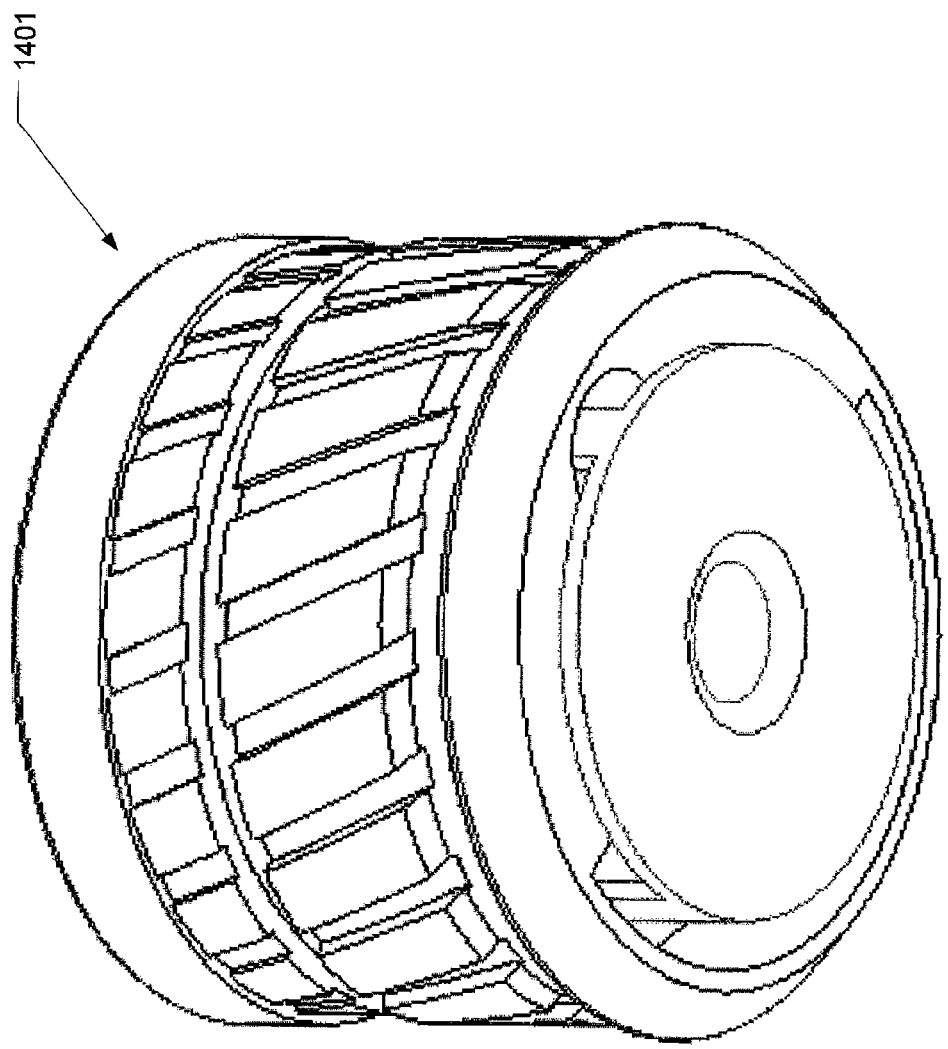
Figure 14F:
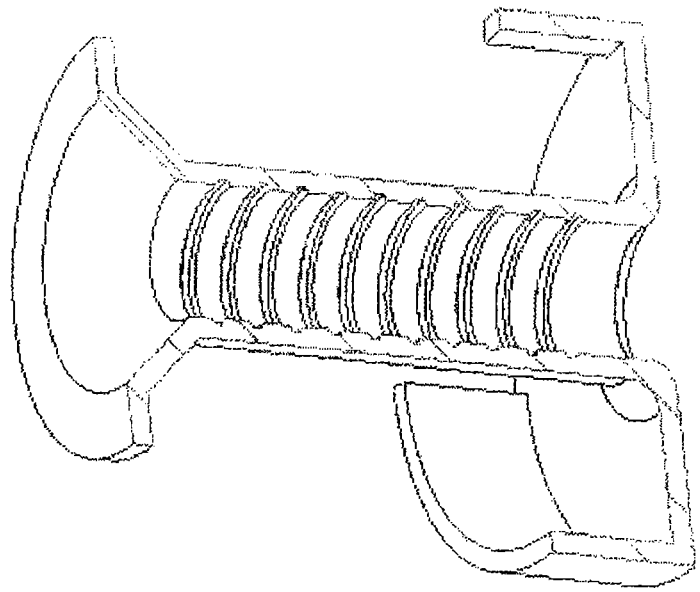
Figure 14E:
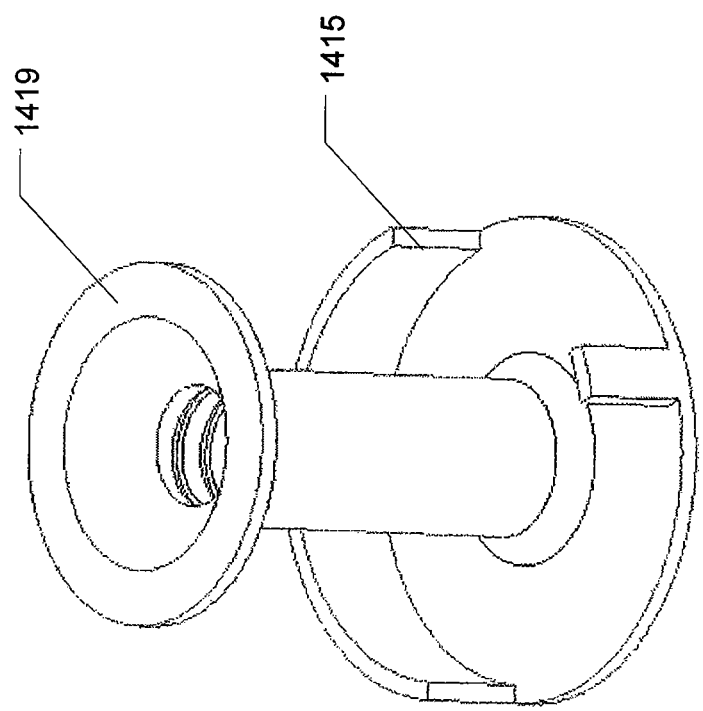
Figure 16C:
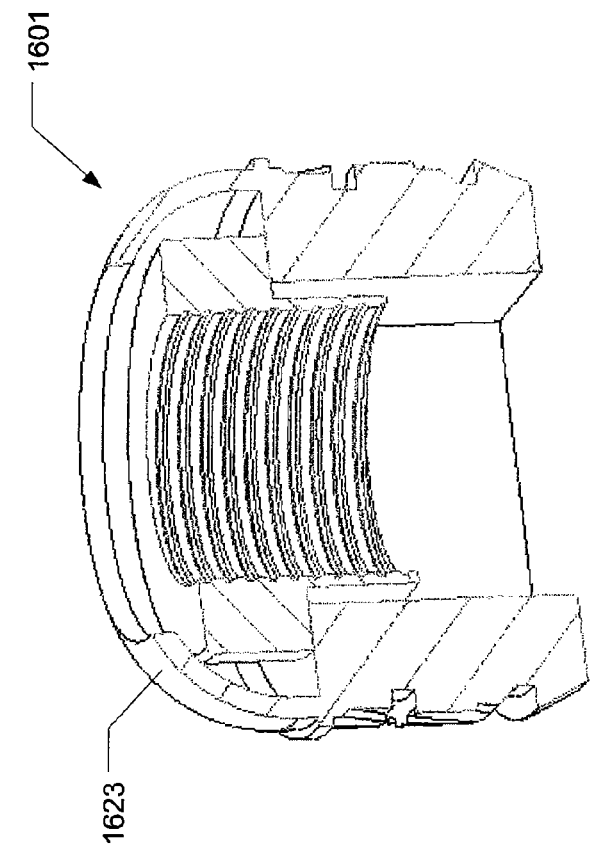
Figure 16B:
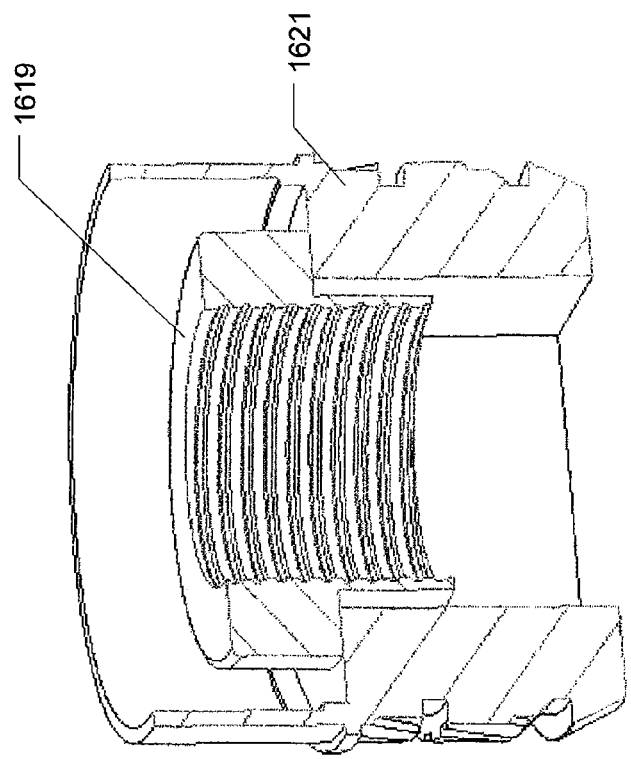
Figure 16D:
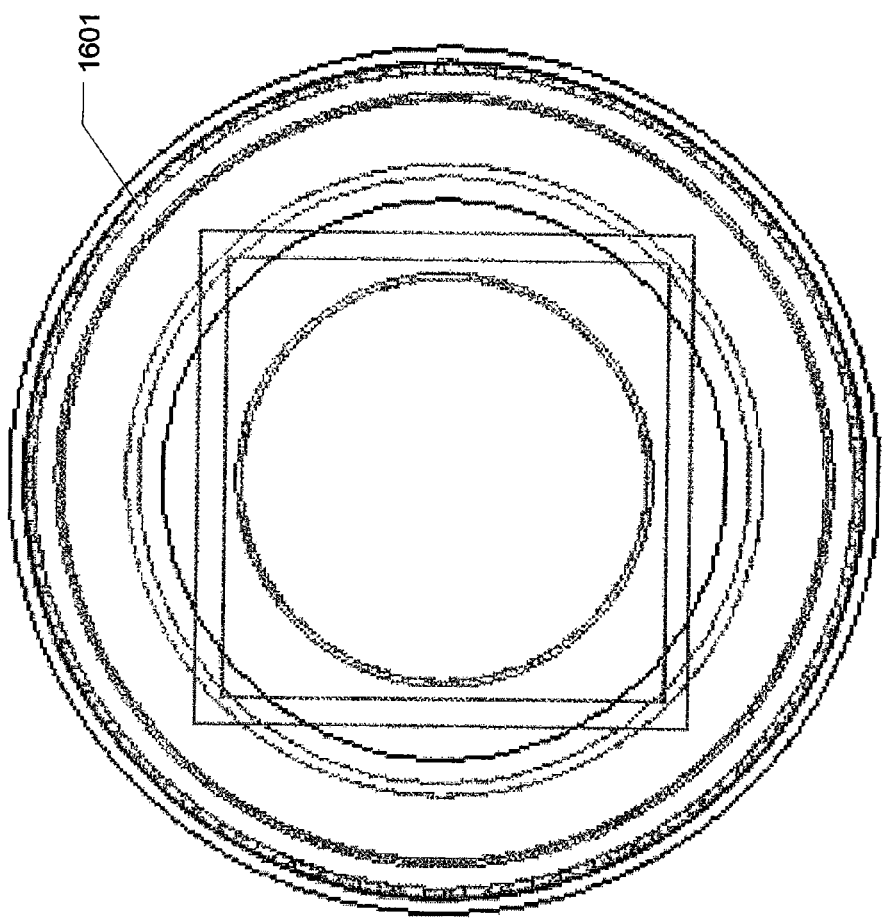
Figure 16F:
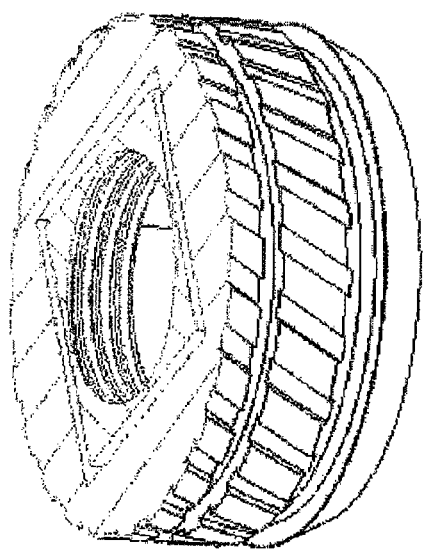
Figure 16E:
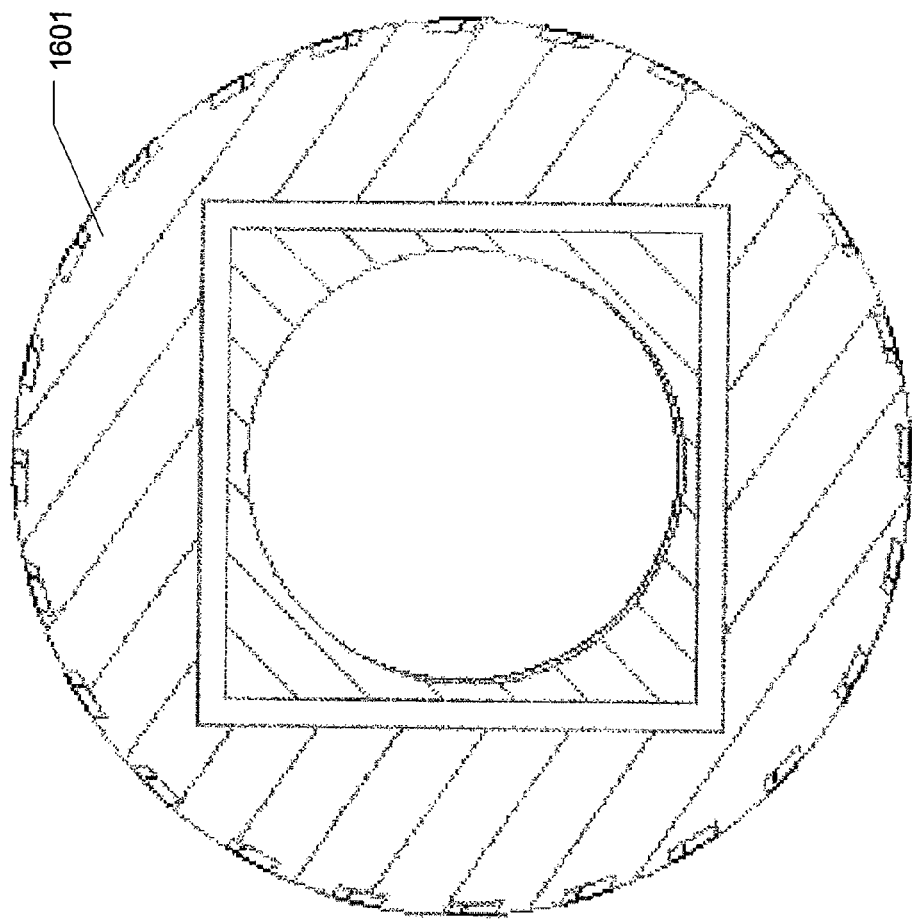
Figure 16H:
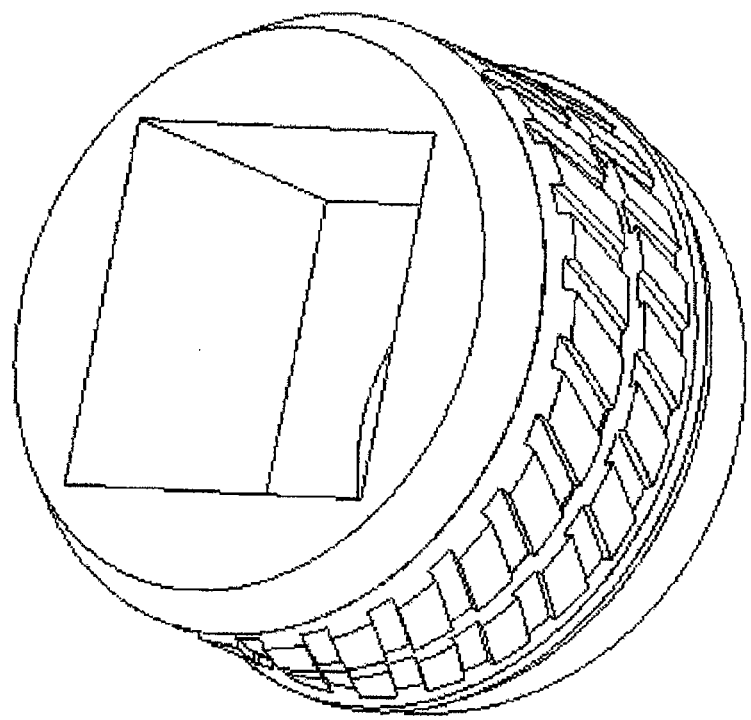
Figure 16G:
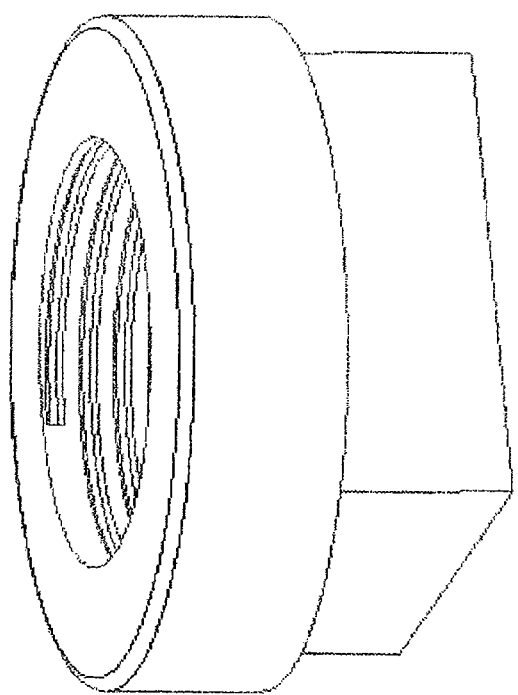

As seen in FIGS. 13a-d, in some embodiments, the plug 1319 may be inserted into a bottom of the body 1311 and a spring 1323 may be inserted into the body 1311 from a top of the body 1311 prior to a top 1325 of the plug 1319 being swaged (FIG. 13a shows un-swagged and FIG. 13b shows a swagged top) into a cone shape in order to trap the plug 1319 and spring 1323 inside the body 1311. As seen in FIG. 16, in some embodiments, the plug 1619 may be placed into body 1621 and a portion 1623 of the body may be swaged into, for example, a dome shape to encapsulate the plug 1619.

In some embodiments, brass inserts ultrasonically welded into a plastic boss and then fastened to the structure using a screw may be used to fasten plastic skins to a mechanical assembly. This may allow for float by means of having the screw being able to move to align to the fixed boss/insert combination. Another method may include a floating female mounting point attached directly to the sheetmetal frame.

Figure 18:
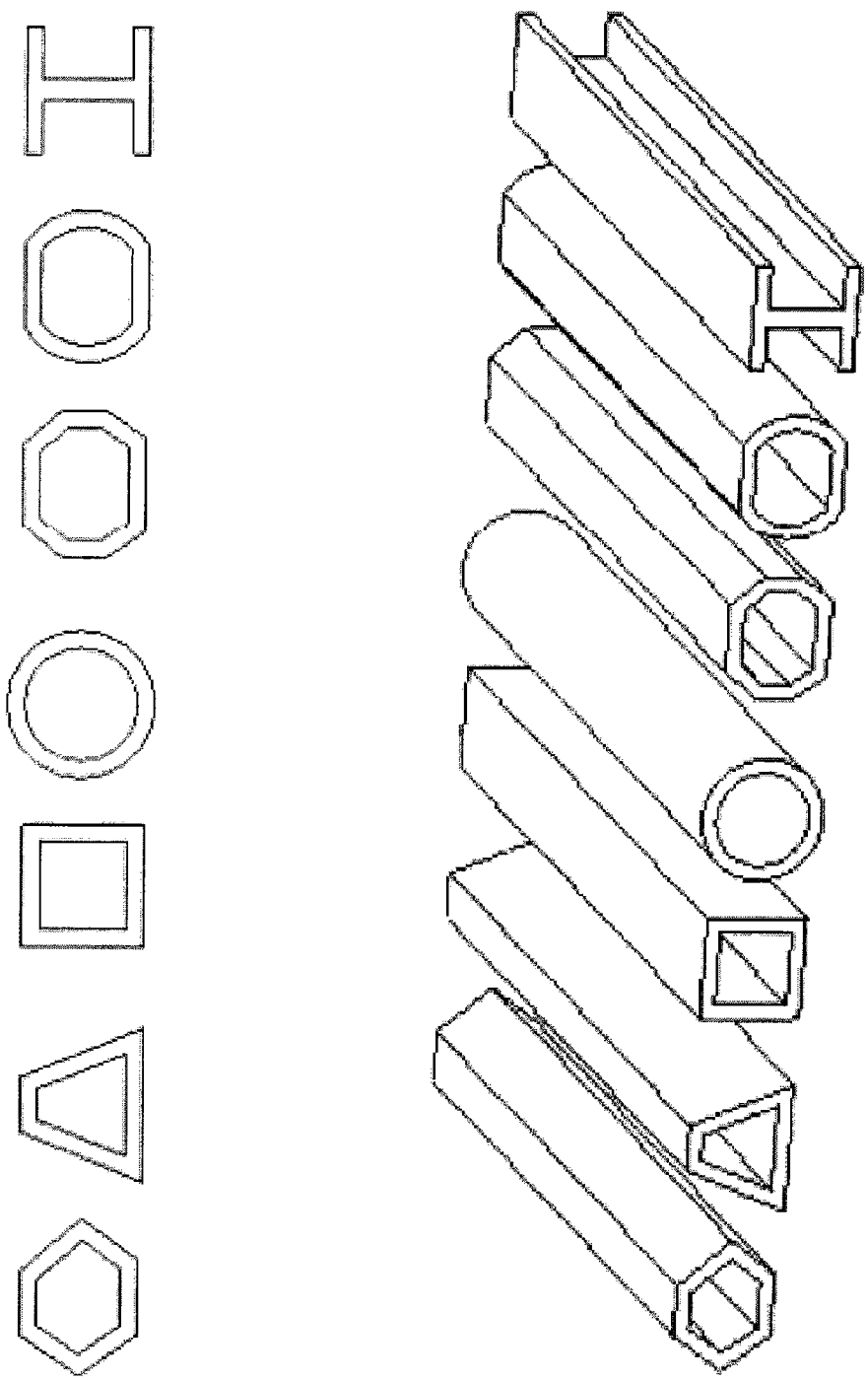
FIG. 18 illustrates various cross sectional shapes for various structural members of the frame system, according to various embodiments.

The frame system 101 may be in the shape of a circle, biloba, ellipse, rectangle, square, octagon, and other geometrical combinations and variations of the aforementioned. As seen in FIG. 18, various cross sectional shapes may be used for the various structural members (e.g., structural members 405*a-e*) of the frame system 101. Various components for the structure may be formed using die forming, hydroforming, mechanical bending, hand layup, etc. In various embodiments, the frame system 101 (e.g., through the interface joints 105) may further provide cable management for internal cables (e.g., through hooks and other cable retaining features that can be coupled to various parts of the frame system), provide mounting locations for fans, improve thermal management by directing air flow of internal machine components, as well as provide other benefits such as lighter weight mounting points and higher tolerances/repeatability over a pure sheet metal structure. In various embodiments, structure members may have different configurations (e.g., made of different materials, have different cross section geometries, etc). For example, structure member 401 includes circular cross section while structure member 403 includes a rectangular cross section. In some embodiments, the rod structure 103 may include round tubes which may be easier to bend while the cross-structural members 601*a-h* may include rectangular cross sections that may be easier for mounting sheet metal (e.g., aesthetic sheet metal skins may be welded along their perimeter to portions of the rectangular cross sections). Hollow cross sections may be used for the rod structure 103 and/or structural members to reduce the overall weight of the frame system 101. In some embodiments, solid cross sections may be used (e.g., solid cross sections of lightweight high strength materials such as a high strength plastic, carbon fiber, or aluminum-titanium allow).

In some embodiments, molding the interface joint 105 may include molding plastic around a performed part (such as a tubular structure member 401 or rectangular structure member 601*a-h*). The preformed part may include a material and/or geometry designed to hold its shape and support characteristics throughout the molding process (e.g., able to withstand pressures and temperatures associated with molding). While some embodiments of the frame system 101 may be made with thermal welding, some embodiments may not include thermal welds (e.g., the frame system 101 may use insert molded joints as the primary attachment mechanism). Frame systems 101 without thermal welds may not have thermal dimensional issues that may be inherent with thermal welding. In some embodiments, the rod structure 103 may be made from steel or aluminum and overmolded with plastic or aluminum utilizing an insert molded investment casting technique. Overmolded aluminum may be used to increase the structural integrity of the structure. (In some embodiments, this form may also be glued together instead of or in addition to the overmolding).

In various embodiments, the rod structure and/or structure members may be made of metal, aluminum, steel, carbon fiber, ceramic, polymers and/or composite materials. Other materials may also be used. Polymers that may be used to create the interface joints may include polyamide, polyphenylene sulfide, polycarbonate, polyvinylchloride, polyarylate, polysurfone, acetal, cellulosics, polyester, melamine, phenolic, urea molding compound, vinyl ester, unsaturated polyester, PC/ABS (polycarbonate/acrylonitrile butadiene styrene), polyetheretherkeytone, liquid crystal polymer, polypropylene, high density polyethylene, bulk molding compound, sheet molding compound, epoxy, and polyurethane. Other materials may also be used.

In some embodiments, the interface joints 105 may be made of electrically conductive materials to assist in grounding the frame. In some embodiments, an epoxy/glue used in addition to the interface joints 105 may also be electrically conductive. While unmodified plastics may be good electrical insulators (e.g., $10^{12}$ to $10^{16}$ ohm-cm) and metals may be good electrical conductors (e.g., $10^{-6}$ to $10^{-1}$ ohm-cm), the electrical conductivity measured as electrical resistivity with the addition of conductive fillers in polymers may be approximately in the range 0.1 to 10,000 ohm-cm. To become electrically conductive, various fillers may be added in various quantities to a polymer used in the interface joints 105. In addition, a glue/epoxy used to bond the rod structure 103/interface joints 105/structural members together may be made electrically conductive using fillers such as metal fibers, carbon fibers, carbon nanotubes, metal coated inorganic nonparticles, carbon powder, and nano-fibers. Additional electrically conductive materials for the interface joints may be selected from polymer grades including (E-Series): E2-conductive LCP (liquid crystal polymer), E3603 and E3605-conductive PA46, E4501 and E4507 Conductive Polycarbonate, E 1201 Conductive Polypropylene, E5101, E5107, E5109-Conductive Polyphenylene Sulfide. In addition to adding conductive fillers, other fillers such as glass fibers, carbon fiber or various other types of fillers may be utilized to increase the mechanical/strength of a composite plastic used for the interface joints 105. Typical flexural modulus of unfilled polymers may be in the range of 300-1000 ksi (thousands of pounds per square inch) and up to 1000 to 7500 ksi for composite polymer types. Other materials with different flexural modulus are also contemplated. In some embodiments, an electrically conductive coating may be applied to one or more components.

Figure 17:
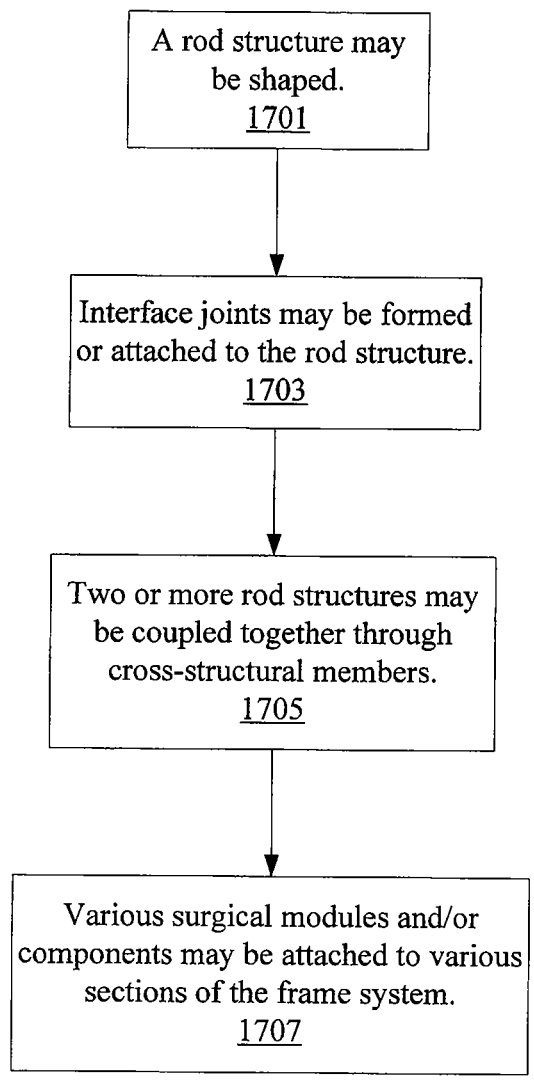
FIG. 17 illustrates a flowchart of a method for assembling a frame system, according to an embodiment.

FIG. 17 illustrates a flowchart of an assembly method for the frame system 101, according to an embodiment. The elements provided in the flowchart are illustrative only. Various provided elements may be omitted, additional elements may be added, and/or various elements may be performed in a different order than provided below.

At 1701, a rod structure 103 may be shaped. In some embodiments, the rod structure 103 may include a continuous bar that is bent into a predetermined shape. In some embodiments, various rod structure members may be shaped and prepared for joining into a larger rod structure 103.

Figure 20A:
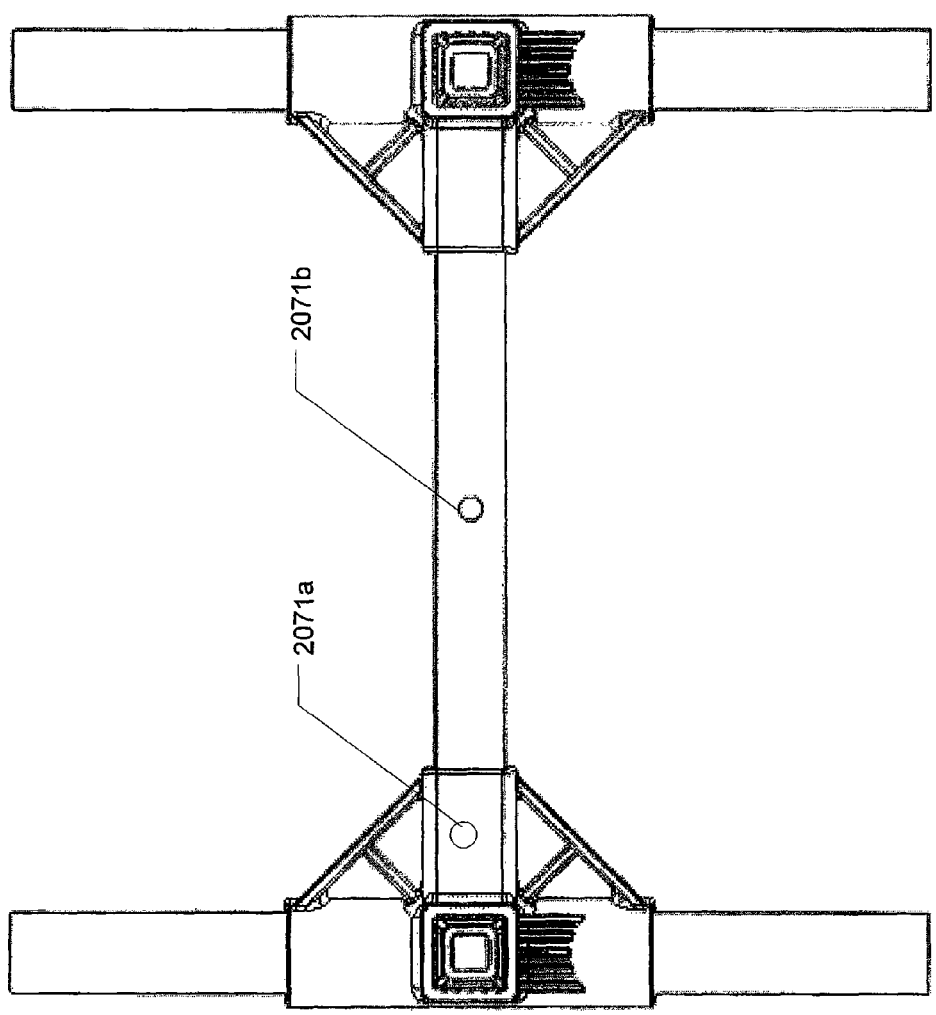
FIGS. 20a-c illustrate additional embodiments of the interface joints.
Figure 20B:
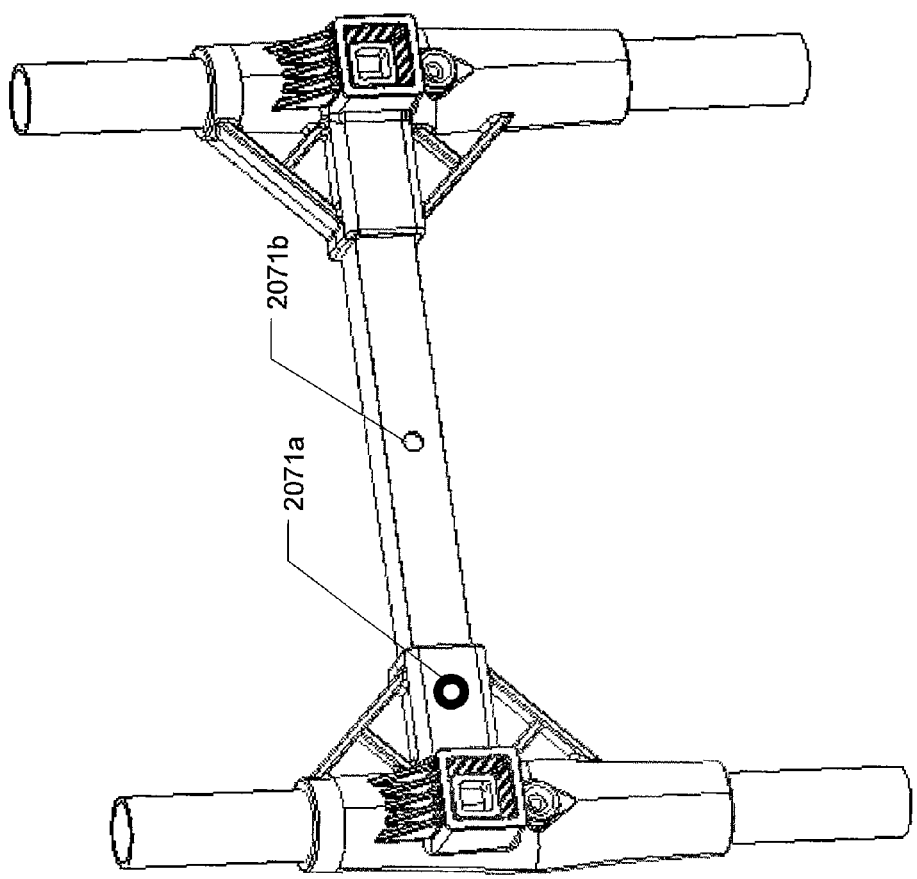
Figure 20C:
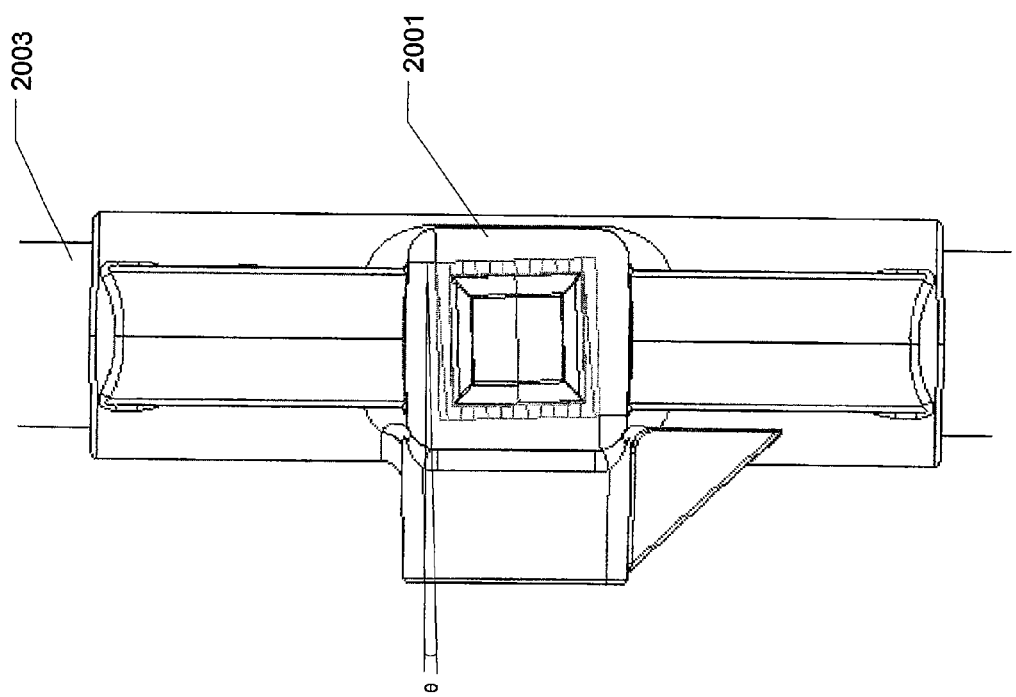

At 1703, interface joints 105 may be formed and/or attached to the rod structure 103. In some embodiments, the interface joints 105 may be molded directly onto the rod structure 103. In some embodiments, the rod structure 103 may include structural members (e.g., cross-face structural members 405*a* and 405*b*) that are attached to each other and/or to the rod structure 103 through the interface joints 105. For example, the interface joints 105 may be formed over a portion of the rod structure 103 and an adjacent structural member to couple the structural member to the rod structure 103. In some embodiments, an end of the structural member may be plugged prior to molding the interface joint 105 over the structural member. In some embodiments, an attachment point (e.g., attachment point 901 in the form of a dimple) may be formed in the rod structure 103 prior to molding the interface joint 105 on the rod structure 103 to better secure the interface joint 105 to the rod structure 103. In some embodiments, attachment point 901 may be formed in rod structure 103 through a moveable indention feature (e.g., a movable cylinder) located inside the injection molding tooling (e.g., see cylinders 905*a,b* in mold halves 903*a,b* shown in FIG. 9*b*). After the mold halves 903*a,b* are placed around the rod structure 103, the cylinders 905*a,b* may pushed forward (e.g., by hydraulics) to create a dimple (or hole) in rod structure 103 and then may be retracted (see movement arrows in FIG. 9*b*). The cylinders 905*a,b* may be activated as soon as the mold was clamped onto the rod structure 103. Activation of the cylinders 905*a,b* may cause the dimpling of structure 103 inside the mold halves 903a,b to create a dimple or hole for mold material to flow into and form attachment point 901. In some embodiments, several of the interface joints 105 for a rod structure may be molded at once (e.g., simultaneously). As seen in FIG. 20c, in some embodiments, one or more joints may be angled (e.g., by angle θ which may be, for example, approximately between 0.5 to 10 degrees) to avoid scraping of a mold along a side of a square member during the opening and closing of the mold halves. For example, if two mold halves come together to form the joint 2001, the side portions of the mold may scrape corresponding sides of a square member (which would be positioned perpendicular to the page) as the molds are clamped to the square member and the brace member 2003 the square member will be attached to. By slanting the square member, the mold sides may come together slightly offset of the square member and the molding material for the joint 2001 may be injected between the mold halves and around the square member and brace member 2003. If the angle θ is 0, then slides or another moving mechanism may be needed in the tooling, which may make the tooling more complicated, more expensive, and possibly require more maintenance.

In some embodiments, several of the interface joints 105 for a rod structure may be molded sequentially. For example, valve gates may be used during injection molding tooling (opening and closing the valve gates to allow through injection molding material may be done in an ordered sequence (e.g., of material flow) across the rod structure). In some embodiments, one or more combinations of barrels and screws may be used to allow for greater flexibility in applying the injection molding material to the rod structure (e.g., through an injection molding tooling) and allow for the use of more than one type of resin to be shot into the tool. For example, the rod structure may include both a more expensive structural grade resin (e.g., with a less expensive panel) and a skin mounting grade resin used in the same structure.

At 1705, two or more rod structures 103 may be coupled together through cross-structural members (e.g., cross-structural members 601a-h). In some embodiments, adhesive may be used in receiving holes (e.g., receiving holes 403a-h) of the interface joints 105 and the cross-structural members 601a-h may be attached to corresponding receiving holes in two or more rod structures 103 to couple the rod structures 103 to each other. In some embodiments, an adhesive may not be used (e.g., the cross-structural members 601a-h may fit in the receiving holes through a friction fit). In some embodiments, the interface joints 105 may be molded over the cross-structural members 601a-h and rod structure 103. FIGS. 20a-b illustrate additional embodiments of the interface joints.

At 1707, various surgical modules and/or components (e.g., aesthetic skins) may be attached to various sections of the frame system 101 that includes the rod structure 103 and structural members coupled together through interface joints 105. For example, sheet metal aesthetic skins may be welded onto square cross section structural members or attached to the structure through one or more fasteners and inserts (e.g., inserts 1301, 1401, or 1601).

In some embodiments, a molding and/or assembly system for the frame system 101 may include one or more processors. The processor may include single processing devices or a plurality of processing devices. Such a processing device may be a microprocessor, controller (which may be a micro-controller), digital signal processor, microcomputer, central processing unit, field programmable gate array, programmable logic device, state machine, logic circuitry, control circuitry, analog circuitry, digital circuitry, and/or any device that manipulates signals (analog and/or digital) based on operational instructions. The memory coupled to and/or embedded in the processors may be a single memory device or a plurality of memory devices. Such a memory device may be a read-only memory, random access memory, volatile memory, non-volatile memory, static memory, dynamic memory, flash memory, cache memory, and/or any device that stores digital information. Note that when the processors implement one or more of its functions via a state machine, analog circuitry, digital circuitry, and/or logic circuitry, the memory storing the corresponding operational instructions may be embedded within, or external to, the circuitry comprising the state machine, analog circuitry, digital circuitry, and/or logic circuitry. The memory may store, and the processor may execute, operational instructions corresponding to at least some of the elements illustrated and described in association with FIG. 17.

Various modifications may be made to the presented embodiments by a person of ordinary skill in the art. Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A floating insert in a polymeric body, comprising:
an outer plug configured with an outer surface that is configured to be received by and fixed inside an aperture of the polymeric body; and
an inner shaped plug with an inner surface that is configured to receive a fastener, wherein the inner shaped plug is configured to float in at least two dimensions relative to the outer plug and wherein the inner shaped plug is configured to not rotate relative to the outer plug;
wherein the outer plug is made of metal that is ultrasonically welded into the aperture;
wherein the metal outer plug comprises at least one groove in the outer surface that receives liquid polymer from the polymeric body as the polymeric body in contact with the metal outer plug liquefies during the ultrasonic welding; and
wherein when the liquid polymer re-solidifies in the at least one groove, the solidified polymer holds the metal outer plug in the aperture of the polymeric body.

2. The floating insert of claim 1, wherein the outer surface of the outer plug has an irregular surface that is configured to be frictionally retained inside the aperture after the outer plug has been inserted into the aperture.

3. The floating insert of claim 1, wherein the outer plug is configured to be received inside the aperture of the polymeric solid body after the outer plug has been heated.

4. The floating insert of claim 1, wherein the inner surface of the inner shaped plug comprises threaded surface that is configured to receive a threaded fastener.

5. The floating insert of claim 1, wherein the inner shaped plug comprises a squared end that fits within a rounded inner chamber of the outer plug and wherein the squared end and rounded inner chamber are sized such that the squared end will not rotate inside the rounded inner chamber.

6. The floating insert of claim 1, wherein one end of the outer plug comprises a rounded outer surface for insertion into the aperture and wherein an opposing side of the outer plug comprises a flat surface with a flat surface aperture.

7. The floating insert of claim 6, wherein the inner surface of the inner shaped plug is configured to receive the fastener through the flat surface aperture of the outer plug.

\* \* \* \* \*